United States Patent
Mahajan et al.

(10) Patent No.: US 11,987,568 B2
(45) Date of Patent: May 21, 2024

(54) ALLOSTERIC INHIBITOR OF WEE1 KINASE

(71) Applicant: H. LEE MOFFITT CANCER CENTER AND RESEARCH INSTITUTE, INC., Tampa, FL (US)

(72) Inventors: Nupam Mahajan, Clayton, MO (US); Nicholas Lawrence, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 136 days.

(21) Appl. No.: 17/265,649

(22) PCT Filed: Aug. 2, 2019

(86) PCT No.: PCT/US2019/044922
§ 371 (c)(1),
(2) Date: Feb. 3, 2021

(87) PCT Pub. No.: WO2020/028814
PCT Pub. Date: Feb. 6, 2020

(65) Prior Publication Data
US 2021/0309630 A1 Oct. 7, 2021

Related U.S. Application Data

(60) Provisional application No. 62/714,351, filed on Aug. 3, 2018.

(51) Int. Cl.
C07D 333/38 (2006.01)
(52) U.S. Cl.
CPC .................. *C07D 333/38* (2013.01)
(58) Field of Classification Search
CPC .................................................. C07D 333/35
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,167,649 A | 12/1992 | Zook | |
| 6,960,648 B2 | 11/2005 | Bonny | |
| 2002/0035243 A1 | 3/2002 | Imfeld et al. | |
| 2002/0120100 A1 | 8/2002 | Bonny | |
| 2003/0032594 A1 | 2/2003 | Bonny | |
| 2017/0000787 A1 | 1/2017 | Sebti et al. | |

FOREIGN PATENT DOCUMENTS

WO 2018136264 A1 7/2018

OTHER PUBLICATIONS

Registry No. 2024558-87-8, File Registry on STN, entered STN Nov. 3, 2016.*
Registry No. 1647838-78-5, File Registry on STN, entered STN Feb. 15, 2015.*
Cancer and Metastasis Reviews (1998), 17(1), 91-106.*
Science (1999), vol. 286, 531-537.*
International Preliminary report on Patentability issued for Application No. PCT/US2019/044922, dated Feb. 18, 2021.
Aarts, M., et al., Forced mitotic entry of S-phase cells as a therapeutic strategy induced by inhibition of WEE1. Cancer Discov, 2012. 2(6): p. 524-39.
Ahmad, A., Y. Takami, and T. Nakayama, WD dipeptide motifs and LXXLL motif of chicken HIRA are essential for interactions with the p48 subunit of chromatin assembly factor-1 and histone deacetylase-2 in vitro and in vivo. Gene, 2004. 342(1): p. 125-36.
Beck, H., et al., Cyclin-Dependent Kinase Suppression by WEE1 Kinase Protects the Genome through Control of Replication Initiation and Nucleotide Consumption. Mol Cell Biol, 2012. 32(20): p. 4226-36.
Do K, Doroshow JH, Kummar S. Wee1 kinase as a target for cancer therapy. Cell Cycle. 2013;12(19):3159-64.
Featherstone, C. and P. Russell, Fission yeast p107wee1 mitotic inhibitor is a tyrosine/serine kinase. Nature, 1991. 349(6312): p. 808-11.
Geenen JJJ, Schellens JHM. Molecular Pathways: Targeting the Protein Kinase Wee1 in Cancer. Clin Cancer Res. 2017;23(16):4540-4544.
Gould, K.L. and P. Nurse, Tyrosine phosphorylation of the fission yeast cdc2+ protein kinase regulates entry into mitosis. Nature, 1989. 342(6245): p. 39-45.
Heintz, N., H.L. Sive, and R.G. Roeder, Regulation of human histone gene expression: kinetics of accumulation and changes in the rate of synthesis and in the half-lives of individual histone mRNAs during the HeLa cell cycle. Mol Cell Biol, 1983. 3(4): p. 539-50.
Hereford, L., S. Bromley, and M.A. Osley, Periodic transcription of yeast histone genes. Cell, 1982. 30(1): p. 305-10.
Hereford, L.M., et al., Cell-cycle regulation of yeast histone mRNA. Cell, 1981. 24(2): p. 367-75.
Hirai, H., et al., Small-molecule inhibition of Wee1 kinase by MK-1775 selectively sensitizes p53-deficient tumor cells to DNA-damaging agents. Molecular cancer therapeutics, 2009. 8(11): p. 2992-3000.
Iorns, E., et al., Integrated functional, gene expression and genomic analysis for the identification of cancer targets. PloS one, 2009. 4(4): p. e5120.
Iwai, A., et al., Combined inhibition of Wee1 and Hsp90 activates intrinsic apoptosis in cancer cells. Cell Cycle, 2012. 11(19): p. 3649-55.

(Continued)

*Primary Examiner* — Rebecca L Anderson
(74) *Attorney, Agent, or Firm* — Meunier Carlin & Curfman LLC

(57) ABSTRACT

Disclosed is a method for selecting a cancer therapeutic for a patient that involves assaying a tumor biopsy sample from the subject to detect PAXIP1 expression, and selecting a WEE1 inhibitor as the cancer therapeutic if PAXIP1 is detected in the tumor biopsy sample.

5 Claims, 18 Drawing Sheets

(56) References Cited

OTHER PUBLICATIONS

Katsuno, Y., et al., Cyclin A-Cdk1 regulates the origin firing program in mammalian cells. Proc Natl Acad Sci U S A, 2009. 106(9): p. 3184-9.
Khuong-Quang, D.A., et al., K27M mutation in histone H3.3 defines clinically and biologically distinct subgroups of pediatric diffuse intrinsic pontine gliomas. Acta Neuropathol, 2012. 124(3): p. 439-47.
Lee, J.S., et al., Codependency of H2B monoubiquitination and nucleosome reassembly on Chd1. Genes Dev, 2012. 26(9): p. 914-9.
Liang, D., et al., Histone dosage regulates DNA damage sensitivity in a checkpoint-independent manner by the homologous recombination pathway. Nucleic acids research, 2012. 40(19): p. 9604-20.
Ma, T., et al., Cell cycle-regulated phosphorylation of p220(NPAT) by cyclin E/Cdk2 in Cajal bodies promotes histone gene transcription. Genes Dev, 2000. 14(18): p. 2298-313.
Mack, G.S., To selectivity and beyond. Nat Biotechnol, 2010. 28(12): p. 1259-66.
Magnussen, G.I., et al., High expression of Wee1 is associated with poor disease-free survival in malignant melanoma: potential for targeted therapy. PLoS One, 2012. 7(6): p. e38254.
Mahajan K, Mahajan NP. WEE1 tyrosine kinase, a novel epigenetic modifier. Trends Genet. 2013;29(7):394-402.
Mahajan, K., et al., H2B Tyr37 phosphorylation suppresses expression of replication-dependent core histone genes. Nat Struct Mol Biol, 2012. 19(9): p. 930-7.
Mahajan, N.P., et al., WEE1 epigenetically modulates 5-hmC levels by pY37-H2B dependent regulation of IDH2 gene expression. Oncotarget, 2017. 8(63): p. 106352-106368.
Marzluff, W.F., et al., The human and mouse replication-dependent histone genes. Genomics, 2002. 80(5): p. 487-98.
Masaki, T., et al., Cyclins and cyclin-dependent kinases: comparative study of hepatocellular carcinoma versus cirrhosis. Hepatology, 2003. 37(3): p. 534-43.
McGowan, C.H. and P. Russell, Cell cycle regulation of human WEE1. Embo J, 1995. 14(10): p. 2166-75.
Medina, R., et al., Epigenetic control of cell cycle-dependent histone gene expression is a principal component of the abbreviated pluripotent cell cycle. Mol Cell Biol, 2012. 32(19): p. 3860-71.
Meeks-Wagner, D. and L.H. Hartwell, Normal stoichiometry of histone dimer sets is necessary for high fidelity of mitotic chromosome transmission. Cell, 1986. 44(1): p. 43-52.
Meeks-Wagner, D., et al., Isolation of two genes that affect mitotic chromosome transmission in S. cerevisiae. Cell, 1986. 44(1): p. 53-63.
Mir, S.E., et al., In silico analysis of kinase expression identifies WEE1 as a gatekeeper against mitotic catastrophe in glioblastoma. Cancer Cell, 2010. 18(3): p. 244-57.
Mollapour, M., et al., Swe1Wee1-dependent tyrosine phosphorylation of Hsp90 regulates distinct facets of chaperone function. Mol Cell, 2010. 37(3): p. 333-43.
Moyal, L., et al., Requirement of ATM-dependent monoubiquitylation of histone H2B for timely repair of DNA double-strand breaks. Molecular cell, 2011. 41(5): p. 529-42.
Murrow, L.M., et al., Identification of WEE1 as a potential molecular target in cancer cells by RNAi screening of the human tyrosine kinome. Breast Cancer Res Treat, 2010. 122(2): p. 347-57.
Oiseth SJ, Aziz MS. Cancer immunotherapy: a brief review of the history, possibilities, and challenges ahead. J Cancer Metastasis Treat. 2017;3:250-61.
Osley, M.A., The regulation of histone synthesis in the cell cycle. Annu Rev Biochem, 1991. 60: p. 827-61.
O'Sullivan, R.J., et al., Reduced histone biosynthesis and chromatin changes arising from a damage signal at telomeres. Nat Struct Mol Biol, 2010. 17(10): p. 1218-25.
Park YJ, Kuen DS, Chung Y. Future prospects of immune checkpoint blockade in cancer: from response prediction to overcoming resistance. Exp Mol Med. 2018; 50:109.
Romanowski, P., et al., Interaction of Xenopus Cdc2 x cyclin A1 with the origin recognition complex. The Journal of biological chemistry, 2000. 275(6): p. 4239-43.
Russell, P. and P. Nurse, Negative regulation of mitosis by wee1+, a gene encoding a protein kinase homolog. Cell, 1987. 49(4): p. 559-67.
Schwartzentruber, J., et al., Driver mutations in histone H3.3 and chromatin remodelling genes in paediatric glioblastoma. Nature, 2012. 482(7384): p. 226-3.
Seligson, D.B., et al., Global histone modification patterns predict risk of prostate cancer recurrence. Nature, 2005. 435(7046): p. 1262-6.
Seligson, D.B., et al., Global levels of histone modifications predict prognosis in different cancers. Am J Pathol, 2009. 174(5): p. 1619-28.
Singh, R.K., et al., Histone levels are regulated by phosphorylation and ubiquitylation-dependent proteolysis. Nat Cell Biol, 2009. 11(8): p. 925-33.
Sirbu, B.M., et al., Analysis of protein dynamics at active, stalled, and collapsed replication forks. Genes Dev, 2011. 25(12): p. 1320-7.
Sobel, R.E., et al., Conservation of deposition-related acetylation sites in newly synthesized histones H3 and H4. Proc Natl Acad Sci U S A, 1995. 92(4): p. 1237-41.
Toyoizumi, Takane, et al. "Combined therapy with chemotherapeutic agents and herpes simplex virus type 1 ICP34. 5 mutant (HSV-1716) in human non-small cell lung cancer." Human gene therapy 10.18 (1999): 3013-3029.
Trujillo, K.M. and M.A. Osley, A Role for H2B Ubiquitylation in DNA Replication. Molecular cell, 2012. 48(5): p. 734-46.
Umansky V, Blattner C, Gebhardt C, Utikal J. The Role of Myeloid-Derived Suppressor Cells (MDSC) in Cancer Progression. Vaccines (Basel). 2016;4(4). pii: E36.
Wang, Z., et al., Combinatorial patterns of histone acetylations and methylations in the human genome. Nat Genet, 2008. 40(7): p. 897-903.
Watanabe, N., M. Broome, and T. Hunter, Regulation of the human WEE1Hu CDK tyrosine 15-kinase during the cell cycle. The EMBO journal, 1995. 14(9): p. 1878-91.
Wu, G., et al., Somatic histone H3 alterations in pediatric diffuse intrinsic pontine gliomas and non-brainstem glioblastomas. Nature genetics, 2012. 44(3): p. 251-3.
Wuarin, J., et al., Stable association of mitotic cyclin B/Cdc2 to replication origins prevents endoreduplication. Cell, 2002. 111(3): p. 419-31.
Wuchty, S., et al., Prediction of Associations between microRNAs and Gene Expression in Glioma Biology. PloS one, 2011. 6(2): p. e14681.
International Search Report and Written Opinion in PCT/US2019/044922, dated Oct. 24, 2019. 8 pages.
Pubmed Compound Record for CID 688263, '1-3-Bis(4-fluorobenzoyl) benzene', US National Library of Medicine, Jul. 7, 2005. pp. 1-11.

* cited by examiner

Libraries around NSC55152 (18-B3)

SG5-111

SG5-124

SG5-159
Renamed as WEIN-159

SG5-172
Renamed as WEIN-172

ALLOSTERIC INHIBITOR OF WEE1 KINASE

CROSS REFERENCE TO RELATED APPLICATIONS

This application is a United States National Phase Patent Application of International Patent Application Number PCT/US2019/044922, filed on Aug. 2, 2019, which claims the benefit of priority to U.S. Provisional Application No. 62/714,351, filed Aug. 3, 2018.

BACKGROUND

Overexpression of WEE1 has been observed in several malignancies, including prostate cancer, hepatocellular carcinoma, luminal and HER-2 positive breast cancers, glioblastoma, and malignant melanoma, where high expression has been shown to correlate with poor disease-free survival. WEE1 is an evolutionarily conserved nuclear tyrosine kinase that is markedly active during the S/G2 phase of the cell cycle. It was first discovered 25 years ago as a cell division cycle (cdc) mutant-wee1-in the fission yeast, *Schizosaccharomyces pombe*. Fission yeast lacking WEE1 are characterized by a smaller cell size, and this phenotype has been attributed to the ability of WEE1 to negatively regulate the activity of cyclin dependent kinase, Cdc2 (Cdc28 in budding yeast and CDK1 in human), in the Cdc2/CyclinB complex.

The central role of WEE1 in integrating various aspects of cell cycle progression, histone synthesis, and genomic stability makes it an important target for cancer treatment. Gene expression profiling of various tumors revealed that the WEE1 kinase is overexpressed in hepatocellular carcinoma (HCC), Glioblastoma multiforme (GBM), luminal, and triple negative breast cancers (TNBC) as well as malignant melanomas. In addition, pharmacologic inhibition by WEE1 inhibitor II or molecular knockdown of WEE1 sensitized PC3 neuroendocrine prostate cancer cells to an Hsp90 inhibitor. Further, WEE1 inhibition by WEE1 inhibitor II, at micromolar concentrations as monotherapy, reduced cell viability, increased DNA damage, and induced apoptosis in various breast cancer cells that represent estrogen-receptor positive, HER-amplified, and triple-negative subtypes, but not in normal mammary epithelial cells and fibroblasts.

WEE1 overexpression and the resultant decrease in histone levels could lead to inefficient chromatin packaging, making the DNA more accessible to the DNA damage repair machinery and promoting radioresistance. The ability of WEE1 to downregulate histone levels could explain why cancer cells become dependent on its epigenetic activity. In addition to acquiring radioresistance, decreased nucleosomal packaging and consequently local alterations in chromatin architecture may activate transcription of pro-proliferative genes or even oncogenes that are otherwise kept in check in normal cells.

Epigenetic inhibitors of WEE1 that would increase histone dosage in actively replicating cancer cells, significantly compromising their proliferation are needed. The compound, compositions, and methods described herein address these and other needs.

SUMMARY

WEE1, a nuclear tyrosine kinase has shown to be an indispensable regulator of cell cycle. It phosphorylates Cdk1 (Cyclin-dependent kinase 1) at the amine acids Tyr15 and Thr14, inhibiting kinase activity of Cdk1 and prevents entry into mitosis until DNA replication has been completed. Role of WEE1 in coordinating transition between DNA replication and mitosis was further accentuated upon recent discovery of its role as a global histone synthesis regulator. WEE1 phosphorylated histone H2B at tyrosine 37 (pY37-H2B) in a distinct spatiotemporal manner and these epigenetic marks were deposited upstream of the histone gene cluster leading to global suppression of histone transcription in late S phase, prior to its entry into G2/M phase. Although, a dual function of WEE1 kinase, a mitotic gatekeeper and a surveyor of chromatin synthesis reveal a new cancer therapeutic option, an inhibitor that specifically overcomes WEE1 epigenetic activity. Indeed, many malignancies including glioblastoma (GBM), melanoma, prostate and triple negative breast cancers exhibit elevated WEE1 expression.

Herein is described a new class of allosteric WEE1 inhibitors. The allosteric WEE1 inhibitors can inhibit WEE1 from binding chromatin and phosphorylating Histone H2B. This can lead to more efficient chromatin packaging and inactivate transcription of oncogenes while increasing transcription of tumor suppressor genes. The new inhibitors do not affect the phosphorylation of Cdc2, thereby avoiding potential side effects in normal cell division when the G2-M checkpoint is removed and cells enter into unscheduled mitosis.

In some examples, the WEE1 inhibitor can include WEIN-159 (WEE1 Epigenetic Inhibitor #159) which overcomes interaction between WEE1 and SIRT7 histone deacetylase, leading to significant increase in H3K18, H3K12 and H3K5 acetylation in the promoters of tumor suppressors. Restoration of H3K18-acetylation upon WEIN-159 treatment not only reinstated expression of tumor suppressors but also suppressed prostate tumor growth, revealing a new therapeutic modality for difficult to treat malignancies. Cell proliferation assays using human prostate cell lines (LNCaP and LAPC4 cells) treated with the allosteric WEE1 inhibitor, WEIN-159, showed $IC_{50}$s of 0.75 µM in LNCaP cells and 0.55 µM in LAPC4 cells. Further, WEIN-159 was also shown to inhibit prostate xenograft tumor growth following subcutaneous implantation of VCaP cells in male SCID mice (n=7), or when LAPC4 cells were implanted subcutaneously in male NOD-SCID mice (n=7). Data showed 58.8% less tumor growth in the VCaP xenograft mice, and 96% less tumor growth in the LAPC4 mice. In addition, oral gavage either with vehicle or WEIN-159 to male NOD-SCID mice, that had LAPC4 cells implanted subcutaneously, showed 50% less tumor growth in the LAPC4 xenograft mice.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows LAPC4 cells were treated with vehicle (DMSO) or compounds (3 µM) for 48 hours, and lysates were immunoprecipitated with pY37-H3B antibodies, followed by immunoblotting with H2B antibodies (top panel). In addition, the lysates were also subjected to immunoblotting with pY15-Cdc2 or actin antibodies (middle and bottom panels). FIG. 2B shows LAPC4 cells were treated with compounds or vehicle (DMSO) for 96 hr and the number of viable cells counted by trypan blue exclusion assay. The number vehicle treated cells were used as control and percent of surviving cells were plotted.

FIG. 3A shows purified full length WEE1 protein was incubated in the reaction buffer containing ATP, in presence of 100 nM epigenetic inhibitors. The reaction mix was then subjected to immunoprecipitated with WEE1 antibodies, followed by immunoblotting with pTyr antibodies (top panel). As a control, purified ACK1 protein was incubated in the reaction buffer containing ATP, in presence of 100 nM epigenetic inhibitors. The reaction mix was then subjected to immunoprecipitated with ACK1 antibodies, followed by immunoblotting with pTyr antibodies (bottom panel). FIG. 3B shows LNCaP cells were treated with vehicle (DMSO) or compounds (10 µM) for 12 hours, and lysates were immunoprecipitated with WEE1 antibodies, followed by immunoblotting with pTyr antibodies (top panel). In addition, the lysates were also subjected to immunoblotting with actin antibodies (bottom panel). FIG. 3C shows LNCaP cells were treated with vehicle (DMSO) or compounds (3 µM) for 12 hours, and lysates were immunoblotted with gamma-H2AX-ser139 antibodies (top panel). In addition, the lysates were also subjected to immunoblotting with actin antibodies (bottom panel).

FIG. 4A shows purified full length WEE1 protein was incubated in the reaction buffer containing ATP, in presence of 100 nM epigenetic inhibitors. The reaction mix was then subjected to immunoprecipitated with WEE1 antibodies, followed by immunoblotting with pTyr antibodies. FIG. 4B shows LNCaP cells were treated with vehicle (DMSO) or compounds (10 µM) for 12 hours, and lysates were immunoprecipitated with pY37-H2B antibodies, followed by immunoblotting with H2B antibodies (top panel). In addition, the lysates were also subjected to immunoblotting with actin antibodies (bottom panel).

FIG. 5C indicated cells were treated with vehicle or compounds (10 uM) for 16 hr. Total genomic DNA was isolated, slot-blotted onto a nitrocellulose membrane, followed by blotting with 5-hmC antibodies (top panels). Blots were also stained with methylene blue, to determine equal loading of DNA (bottom panel).

FIG. 7A shows LNCaP cells were treated with vehicle compounds (10 µM) for 24 hours, and lysates were subjected to immunoblotting with pY15-Cdc2 antibodies (top panel) and actin antibodies (bottom panel). In addition, lysates were immunoprecipitated with pY37-H2B antibodies, followed by immunoblotting with H2B antibodies (middle panel). FIG. 7B shows LNCaP cells were treated with vehicle (DMSO) or compounds (10 µM) for 24 hours, and lysates were immunoprecipitated with WEE1 antibodies, followed by immunoblotting with pTyr antibodies (top panel). The lysates were also subjected to immunoblotting with pY15-Cdc2 antibodies and were immunoprecipitated with pY37-H2B antibodies, followed by immunoblotting with H2B antibodies (middle panels). In addition, the lysates were also subjected to immunoblotting with H2B antibodies (bottom panel). FIG. 7C shows B16 cells were treated with vehicle (DMSO) or compounds (10 µM) for 24 hours, and lysates were immunoprecipitated with WEE1 antibodies, followed by immunoblotting with pTyr antibodies (top panel). The lysates were also subjected to immunoblotting with pY15-Cdc2 antibodies and were immunoprecipitated with pY37-H2B antibodies, followed by immunoblotting with H2B antibodies (middle panels). In addition, the lysates were also subjected to immunoblotting with actin antibodies (bottom panel).

FIG. 8A shows LNCaP cells were treated with vehicle or compounds (5 or 10 uM) for 16 hr. Total RNA was isolated followed by qRT-PCR with histone H3 and actin primers. FIG. 8B shows LAPC4 cells were treated with vehicle or compounds (3.5 uM) for 48 hr. Total RNA was isolated followed by qRT-PCR with histone H3 and actin primers.

FIG. 9A shows LNCaP cells were treated with compounds or vehicle (DMSO) for 96 hr and the number of viable cells counted by trypan blue exclusion assay. The number of vehicle treated cells were used as control and percent of surviving cells were plotted. FIG. 9B shows LAPC4 cells were treated with compounds or vehicle (DMSO) for 96 hr and the number of viable cells counted by trypan blue exclusion assay. The number vehicle treated cells were used as control and percent of surviving cells were plotted.

FIG. 11A shows biotinylated WEIN-159 and WEIN-172 immobilized onto streptavidin beads were incubated with LNCaP cell lysates followed by immunoblotting with WEE1 antibodies. FIG. 11B shows MYC-tagged WEE1 deletion constructs were generated. FIGS. 11C-11E show biotinylated WEIN-159 and WEIN-172 immobilized onto streptavidin beads were incubated with lysates prepared from HEK293T cells transfected with MYC-tagged WEE1 deletion constructs, followed by immunoblotting with MYC antibodies.

FIGS. 16A-16D show restoration of H4K5 and H3K12 epigenetic marks by epigenetic inhibitor of WEE1 kinase.

FIG. 21 shows MDSC suppression by WEIN-159A.

DETAILED DESCRIPTION

General Definitions

Figure 1:
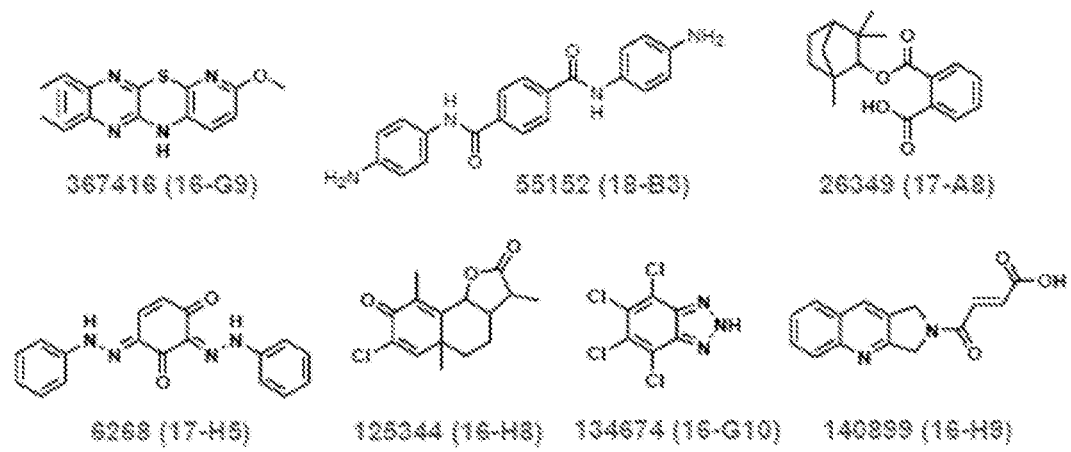
FIG. 1 shows structures of 'hits' identified in WEE1 epigenetic inhibitor screen. The compounds are divided in 3 categories based on their activity.
Figure 1:
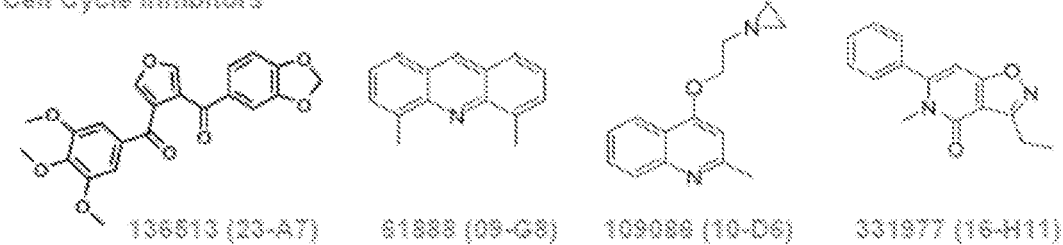
Figure 1:
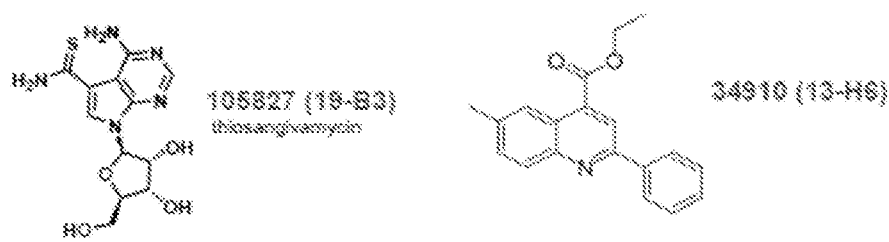

The term "subject" refers to any individual who is the target of administration or treatment. The subject can be a vertebrate, for example, a mammal. Thus, the subject can be a human or veterinary patient. The term "patient" refers to a subject that is under the care of a treating clinician (e.g., physician).

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "palliative" refers to a treatment that is designed to relieve symptoms (e.g., reduce pain or discomfort) without having a curative effect on the underlying disease or cause (e.g., cell growth and metastasis).

The term "remedial" refers to a treatment that is designed to have a curative effect on the underlying disease or cause (e.g., cell growth and metastasis) and not just to relieve symptoms.

The term "neoplastic cells" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

The term "tumor" or "neoplasm" refers to an abnormal mass of tissue containing neoplastic cells. Neoplasms and tumors may be benign, premalignant, or malignant.

The term "cancer" or "malignant neoplasm" refers to a cell that displays uncontrolled growth, invasion upon adjacent tissues, and often metastasis to other locations of the body.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substitutent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

"Aryl", as used herein, refers to 5-, 6- and 7-membered aromatic rings. The ring can be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that can include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure can also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl" or "aryl-alkyl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, (C$_1$-C$_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazolyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula: —NR$_9$R$_{10}$ or NR$_9$R$_{10}$R'$_{10}$, wherein R$_9$, R$_{10}$, and R'$_{10}$ each independently represent a hydrogen, an alkyl, an alkenyl, —(CH$_2$)$_m$—R'$_8$ or R$_9$ and R$_{10}$ taken together with the N atom to which they are attached complete a heterocycle having from 4 to 8 atoms in the ring structure; R'$_8$ represents an aryl, a cycloalkyl, a cycloalkenyl, a heterocycle or a polycycle; and m is zero or an integer in the range of 1 to 8. In some embodiments, only one of R$_9$ or R$_{10}$ can be a carbonyl, e.g., R$_9$, R$_{10}$ and the nitrogen together do not form an imide. In some embodiments, the term "amine" does not encompass amides, e.g., wherein one of R$_9$ and R$_{10}$ represents a carbonyl. In some embodiments, R$_9$ and R$_{10}$ (and optionally R'$_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R$_9$ and R$_{10}$ is an alkyl group.

The term "amide" is art-recognized as an amino-substituted carbonyl and includes a moiety that can be represented by the general formula —CONR$_9$R$_{10}$ wherein R$_9$ and R$_{10}$ are as defined above.

"Halogen", as used herein, refers to fluorine, chlorine, bromine, or iodine.

The term "carboxylic acid" as used herein is represented by the formula —C(O)OH. A "carboxylate" as used herein is represented by the formula —C(O)O$^-$.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN

The term "azido" as used herein is represted by the formula —N$_3$.

The term "sulfonyl" is used herein to refer to the sulfo-oxo group represented by the formula —S(O)$_2$A$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" or "thio" as used herein is represented by the formula —SH.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures. A number of embodiments of the invention have been described. Nevertheless, it will be understood that various modifications may be made without departing from the spirit and scope of the invention. Accordingly, other embodiments are within the scope of the following claims.

Disclosed are WEE1 epigenetic inhibitors. The WEE1 epigenetic inhibitors are compounds having a structure represented by Formula:

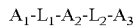

wherein $A_1$, $A_2$, and $A_3$ are independently selected from a substituted or unsubstituted cycloalkyl, a substituted or unsubstituted heterocycloalkyl, a substituted or unsubstituted cycloalkenyl, a substituted or unsubstituted heterocycloalkenyl, a substituted or unsubstituted aryl, or a substituted or unsubstituted heteroaryl, wherein $A_1$, $A_2$, or $A_3$ are independently substituted with substituted or unsubstituted hydroxyl, substituted or unsubstituted halogen, substituted or unsubstituted amine, substituted or unsubstituted nitro, substituted or unsubstituted cyano, substituted or unsubstituted amide, substituted or unsubstituted ester, substituted or unsubstituted thio, substituted or unsubstituted carboxyl, substituted or unsubstituted carbonyl, substituted or unsubstituted $C_{1-6}$ alkoxy, substituted or unsubstituted $C_{1-6}$ haloalkoxy, substituted or unsubstituted $C_{1-6}$ alkylthio, substituted or unsubstituted $C_{1-6}$ haloalkylthio, substituted or unsubstituted $C_{1-6}$ alkylamine, substituted or unsubstituted $C_{1-6}$-alkyl, substituted or unsubstituted $C_{1-6}$-alkenyl, substituted or unsubstituted $C_{1-6}$-alkylester, substituted or unsubstituted $C_1$-$C_6$ alkyl halide, substituted or unsubstituted cycloalkyl, or substituted or unsubstituted aryl; and $L_1$ and $L_2$ are linkers independently selected from selected from the group consisting of —SO$_2$, —SO$_2$R'; SO$_2$R'R", —SO$_2$NR'R"; —SO$_2$NR'R"C(=O); —NR'SO$_2$R"; —R'SO$_2$NR'R'''; —C(=O); —C(=O)R'; —OC(=O)R'; —C(=O)NR'R"; —NR'C(=O)R"; —NR'C(=O)R"C(=O); —OR'; —NR'R"; —SR'; —N$_3$—C(=O)OR'; —O(CR'R")$_r$C(=O)R'; —O(CR'R")$_r$NR"C(=O)R'; —O(CR'R")$_r$NR"SO$_2$R'; —OC(=O)NR'R"; —NR'C(=O)OR"; and substituted or unsubstituted $C_1$-$C_6$ aliphatic alkyl, wherein R', R", and R" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6.

In some embodiments, the compound can have a structure represented by Formula I:

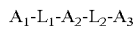 Formula I wherein $A_1$, $A_2$, and $A_3$ are independently selected from a substituted or unsubstituted cycloalkyl, a substituted or unsubstituted heterocycloalkyl, a substituted or unsubstituted cycloalkenyl, a substituted or unsubstituted heterocycloalkenyl, a substituted or unsubstituted aryl, or a substituted or unsubstituted heteroaryl, wherein $A_1$, $A_2$, and $A_3$ are independently substituted with hydroxyl, halogen, alkyl halide, amine, alkyl amine, substituted or unsubstituted nitro, substituted or unsubstituted cyano, substituted or unsubstituted amide, substituted or unsubstituted ester, substituted or unsubstituted thio, substituted or unsubstituted carboxyl, substituted or unsubstituted carbonyl, substituted or unsubstituted alkyl, substituted or unsubstituted alkenyl, substituted or unsubstituted alkoxy, amine$C_{1-6}$-alkylester, substituted or unsubstituted cycloalkyl, or substituted or unsubstituted aryl; and $L_1$ and $L_2$ are linkers independently selected from selected from the group consisting of —SO$_2$, —SO$_2$R'; —SO$_2$R'R", —SO$_2$NR'R"; —SO$_2$NR'R"C(=O); —NR'SO$_2$R"; —R'SO$_2$NR'R'''; —C(=O); —C(=O)R'; —OC(=O)R'; —C(=O)NR'R"; —NR'C(=O)R"; —NR'C(=O)R"C(=O); —OR'; —NR'R"; —SR'; —N$_3$—C(=O)OR'; —O(CR'R")$_r$C(=O)R'; —O(CR'R")$_r$NR"C(=O)R'; —O(CR'R")$_r$NR"SO$_2$R'; —OC(=O)NR'R"; —NR'C(=O)OR"; and substituted or unsubstituted $C_1$-$C_6$ aliphatic alkyl, wherein R', R", and R" are individually selected from null, hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6.

In some embodiments of Formula I, $A_1$ and $A_3$ can be independently selected from a substituted or unsubstituted aryl or a substituted or unsubstituted heteroaryl. For example, $A_1$ and $A_3$ can be independently substituted with $C_{1-6}$ alkoxy, halogen, $C_{1-6}$ haloalkoxy, thiol, $C_{1-6}$ alkylthio, $C_{1-6}$ haloalkylthio, amine, $C_{1-6}$ alkylamine, $C_{1-6}$-alkyl, $C_{2-6}$-alkenyl, $C_{1-6}$-alkylester, or $C_1$-$C_6$ alkyl halide.

The compounds disclosed herein can have a structure represented by Formula I-A:

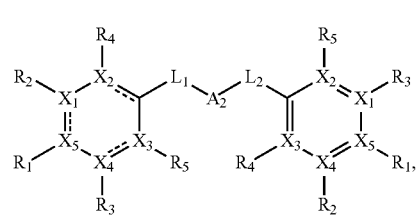 Formula I-A wherein $A_2$ is selected from a substituted or unsubstituted cycloalkyl, a substituted or unsubstituted heterocycloalkyl, a substituted or unsubstituted cycloalkenyl, a substituted or unsubstituted heterocycloalkenyl, a substituted or unsubstituted aryl, or a substituted or unsubstituted heteroaryl, wherein $A_2$ is optionally substituted with hydroxyl, halogen, alkyl halide, amine, alkyl amine, substituted or unsubstituted nitro, substituted or unsubstituted cyano, substituted or unsubstituted amide, substituted or unsubstituted ester, substituted or unsubstituted thio, substituted or unsubstituted carboxyl, substituted or unsubstituted carbonyl, substituted or unsubstituted alkyl, substituted or unsubstituted alkenyl, substituted or unsubstituted alkoxy, $C_{1-6}$-alkylester, substituted or unsubstituted cycloalkyl, or substituted or unsubstituted aryl;

$L_1$ and $L_2$ are linkers independently selected from selected from the group consisting of —SO$_2$, —SO$_2$R'; —SO$_2$R'R", —SO$_2$NR'R"; —SO$_2$NR'R"C(=O); —NR'SO$_2$R"; —R'SO$_2$NR'R'''; —C(=O); —C(=O)R'; —OC(=O)R'; —C(=O)NR'R"; —NR'C(=O)R";

—NR'C(=O)R"C(=O); —OR'; —NR'R"; —SR'; —N₃—C(=O)OR'; —O(CR'R")ᵣC(=O)R'; —O(CR'R")ᵣNR"C(=O)R'; —O(CR'R")ᵣNR"SO₂R'; —OC(=O)NR'R"; —NR'C(=O)OR"; and substituted or unsubstituted C₁-C₆ aliphatic alkyl, wherein R', R", and R" are individually selected from null, hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

R₁, independently for each occurrence, is selected from hydroxyl, halogen, thiol, C₁-C₆ alkyl, C₁-C₆ alkyl halide, C₁₋₆ alkoxy, amine, C₁₋₆ alkylamine, C₁₋₆ alkylthio, C₁₋₆ haloalkoxy, C₁₋₆ haloalkylthio, C₂₋₆-alkenyl, C₁₋₆-alkylester, or a salt thereof;

R₂ and R₃, independently for each occurrence, are independently selected from hydrogen, hydroxyl, C₁-C₆ alkyl, halogen, amine, C₁₋₆ alkylamine, or a salt thereof;

R₄ and R₅, independently for each occurrence, are independently selected from hydrogen, hydroxyl, C₁-C₆ alkyl, halogen, amine, C₁₋₆ alkylamine, or a salt thereof;

X₁ to X₅, independently for each occurrence, are independently selected from C, CH, or N; and ----- represents a bond that is present or absent.

In some embodiments of Formulas I and I-A, the bond ----- is present for each occurrence.

The compounds disclosed herein can have a structure represented by Formula I-A-1:

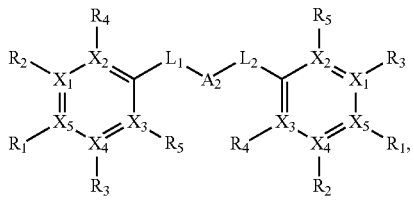

Formula I-A-1 wherein A₂ is selected from imidazole, pyrazole, thiazole, isothiazole, azathiozole, oxothiazole, oxazine, oxazoline, oxazaborole, dithiozoles, triazole, selenozole, oxahosphole, pyrrole, borole, furan, thiphene, phosphole, pentazole, indole, indoline, oxazole, isothirazole, tetrazole, benzofuran, dibenzofuran, benzothiophene, dibenzothoiphene, thiadiazole, pyrdine, pyrimidine, pyrazine, pyridazine, piperazine, piperidine, morpholine, pyran, annoline, phthalazine, quinazoline, or quinoxaline, wherein A₂ is optionally substituted with hydroxyl, halogen, alkyl halide, amine, alkyl amine, substituted or unsubstituted nitro, substituted or unsubstituted cyano, substituted or unsubstituted amide, substituted or unsubstituted ester, substituted or unsubstituted thio, substituted or unsubstituted carboxyl, substituted or unsubstituted carbonyl, substituted or unsubstituted alkyl, substituted or unsubstituted alkenyl, substituted or unsubstituted alkoxy, C₁₋₆-alkylester, substituted or unsubstituted cycloalkyl, or substituted or unsubstituted aryl;

L₁ and L₂ are linkers independently selected from selected from the group consisting of —SO₂, —SO₂R'; —SO₂R'R", —SO₂NR'R"; —SO₂NR'R"C(=O); —NR'SO₂R"; —R'SO₂NR'"; —C(=O); —C(=O)R'; —OC(=O)R'; —C(=O)NR'R"; —NR'C(=O)R"; —NR'C(=O)R"C(=O); —OR'; —NR'R"; —SR'; —N₃—C(=O)OR'; —O(CR'R")ᵣC(=O)R'; —O(CR'R")ᵣNR"C(=O)R'; —O(CR'R")ᵣNR"SO₂R'; —OC(=O)NR'R"; —NR'C(=O)OR"; and substituted or unsubstituted C₁-C₆ aliphatic alkyl, wherein R', R", and R" are individually selected from a bond, hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

R₁, independently for each occurrence, is selected from hydroxyl, halogen, thiol, C₁-C₆ alkyl, C₁-C₆ alkyl halide, C₁₋₆ alkoxy, amine, C₁₋₆ alkylamine, C₁₋₆ alkylthio, C₁₋₆ haloalkoxy, C₁₋₆ haloalkylthio, C₂₋₆-alkenyl, C₁₋₆-alkylester, or a salt thereof;

R₂ and R₃, independently for each occurrence, are independently selected from hydrogen, hydroxyl, C₁-C₆ alkyl, halogen, amine, C₁₋₆ alkylamine, or a salt thereof; and R₄ and R₅, independently for each occurrence, are independently selected from hydrogen, hydroxyl, C₁-C₆ alkyl, halogen, amine, C₁₋₆ alkylamine, or a salt thereof; and X₁ to X₅, independently for each occurrence, are independently selected from C, CH, or N.

In some embodiments of Formulas I, I-A, and I-A-1, X₁ to X₅, independently for each occurrence, are independently selected from C or CH. For example, X₁ to X₅ can be C. In some examples, at least one of X₁ to X₅, independently for each occurrence, can be N.

The compounds disclosed herein can have a structure represented by Formula I-B:

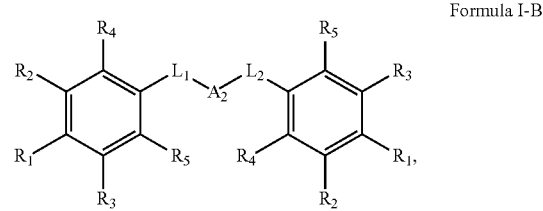

Formula I-B wherein A₂ is selected from a substituted or unsubstituted cycloalkyl, a substituted or unsubstituted heterocloalkyl, a substituted or unsubstituted cycloalkenyl, a substituted or unsubstituted heterocycloalkenyl, a substituted or unsubstituted aryl, or a substituted or unsubstituted heteroaryl, wherein A₂ is optionally substituted with hydroxyl, halogen, alkyl halide, amine, alkyl amine, substituted or unsubstituted nitro, substituted or unsubstituted cyano, substituted or unsubstituted amide, substituted or unsubstituted ester, substituted or unsubstituted thio, substituted or unsubstituted carboxyl, substituted or unsubstituted carbonyl, substituted or unsubstituted alkyl, substituted or unsubstituted alkenyl, substituted or unsubstituted alkoxy, $C_{1-6}$-alkylester, substituted or unsubstituted cycloalkyl, or substituted or unsubstituted aryl;

$L_1$ and $L_2$ are linkers independently selected from selected from the group consisting of —$SO_2$, —$SO_2R'$; —$SO_2R'R''$; —$SO_2NR'R''$; —$SO_2NR'R''C(=O)$; —$NR'SO_2R''$; —$R'SO_2NR'R'''$; —$C(=O)$; —$C(=O)R'$; —$OC(=O)R'$; —$C(=O)NR'R''$; —$NR'C(=O)R''$; —$NR'C(=O)R''C(=O)$; —$OR'$; —$NR'R''$; —$SR'$; —$N_3$—$C(=O)OR'$; —$O(CR'R'')_rC(=O)R'$; —$O(CR'R'')_rNR''C(=O)R'$; —$O(CR'R'')_rNR''SO_2R'$; —$OC(=O)NR'R''$; —$NR'C(=O)OR''$; and substituted or unsubstituted $C_1$-$C_6$ aliphatic alkyl, wherein R', R'', and R''' are individually selected from null, hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R_1$, independently for each occurrence, is selected from hydroxyl, halogen, thiol, $C_1$-$C_6$ alkyl, $C_1$-$C_6$ alkyl halide, $C_{1-6}$ alkoxy, amine, $C_{1-6}$ alkylamine, $C_{1-6}$ alkylthio, $C_{1-6}$ haloalkoxy, $C_{1-6}$ haloalkylthio, $C_{2-6}$-alkenyl, $C_{1-6}$-alkylester, or a salt thereof;

$R_2$ and $R_3$, independently for each occurrence, are independently selected from hydrogen, hydroxyl, $C_1$-$C_6$ alkyl, halogen, amine, $C_{1-6}$ alkylamine, or a salt thereof; and $R_4$ and $R_5$, independently for each occurrence, are independently selected from hydrogen, hydroxyl, $C_1$-$C_6$ alkyl, halogen, amine, $C_{1-6}$ alkylamine, or a salt thereof.

In some embodiments of Formulas I, I-A, I-A-1, and I-B, $A_2$ can be a substituted or unsubstituted heteroaryl. For example, $A_2$ can be a substituted or unsubstituted imidazole, pyrazole, thiazole, isothiazole, azathiozole, oxothiazole, oxazine, oxazoline, oxazaborole, dithiozole, triazole, selenozole, oxahosphole, pyrrole, borole, furan, thiophene, phosphole, pentazole, indole, indoline, oxazole, isothirazole, tetrazole, benzofuran, dibenzofuran, benzothiophene, dibenzothoiphene, thiadiazole, pyrdine, pyrimidine, pyrazine, pyridazine, piperazine, piperidine, morpholine, pyran, annoline, phthalazine, quinazoline, or quinoxaline. In some examples, $A_2$ can be an unsubstituted thiophene.

In some embodiments of Formulas I, I-A, I-A-1, and I-B, $A_2$ can be substituted with $C_{1-6}$ alkoxy, $C_{1-6}$-alkyl, or $C_1$-$C_6$ alkyl halide. For example, $A_2$ can be substituted with $C_{1-6}$-alkyl. In some embodiments, $A_2$ is unsubstituted.

In some embodiments of Formulas I, I-A, I-A-1, and I-B, $R_1$, independently for each occurrence, can be selected from amine, $C_{1-6}$ alkylamine, or a salt thereof. In some examples, each occurrence of $R_1$ can be the same. In other examples, each occurrence of $R_1$ can be different.

In some embodiments of Formulas I, I-A, I-A-1, and I-B, $R_2$, independently for each occurrence, can be selected from hydrogen, hydroxyl, halogen, amine, or a salt thereof. For example, $R_2$, independently for each occurrence, can be selected from hydrogen. In some examples, each occurrence of $R_2$ can be the same. In other examples, each occurrence of $R_2$ can be different.

In some embodiments of Formulas I, I-A, I-A-1, and I-B, $R_3$, independently for each occurrence, can be selected from hydrogen, hydroxyl, halogen, amine, or a salt thereof. For example, $R_3$, independently for each occurrence, can be selected from hydrogen. In some examples, each occurrence of $R_3$ can be the same. In other examples, each occurrence of $R_3$ can be different.

In some embodiments of Formulas I, I-A, I-A-1, and I-B, $R_4$, independently for each occurrence, can be selected from hydrogen, hydroxyl, halogen, amine, or a salt thereof. For example, $R_4$, independently for each occurrence, can be selected from hydrogen. In some examples, each occurrence of $R_4$ can be the same. In other examples, each occurrence of $R_4$ can be different.

In some embodiments of Formulas I, I-A, I-A-1, and I-B, $R_4$, independently for each occurrence, can be selected from hydrogen, hydroxyl, halogen, amine, or a salt thereof. For example, $R_4$, independently for each occurrence, can be selected from hydrogen. In some examples, each occurrence of $R_4$ can be the same. In other examples, each occurrence of $R_4$ can be different.

In some examples, $R_4$ and $R_5$, for each occurrence, is hydrogen.

In some embodiments of Formulas I, I-A, I-A-1, and I-B, $L_1$ and $L_2$ are independently selected from selected from the group consisting of —$SO_2NR'R''$; —$NR'SO_2R''$; —$R'SO_2NR'R'''$; —$C(=O)R'$; —$OC(=O)R'$; —$C(=O)NR'R''$; —$NR'C(=O)R''$; —$NR'C(=O)R''C(=O)$; —$OC(=O)NR'R''$; —$NR'C(=O)OR''$; wherein R', R'', and R''' are individually selected from a bond, hydrogen; or substituted or unsubstituted alkyl. For example, $L_1$ and $L_2$ can be independently selected from selected from the group consisting of —$C(=O)NR'R''$; wherein R', R'', and R''' are individually selected from a bond, hydrogen; or unsubstituted alkyl.

The compounds disclosed herein can have a structure below:

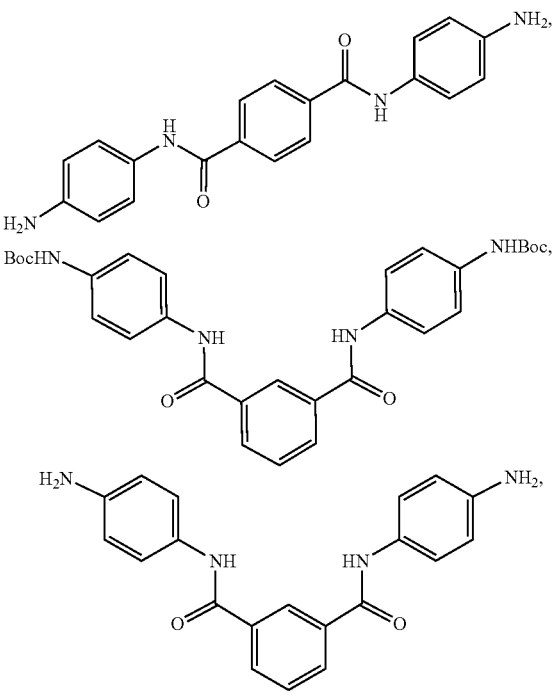

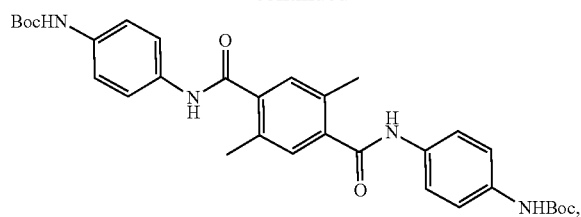
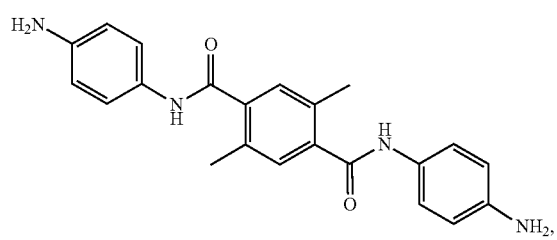
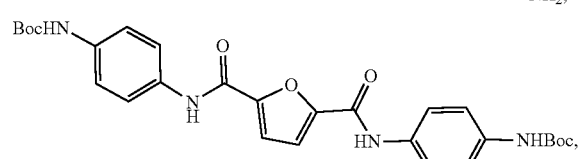
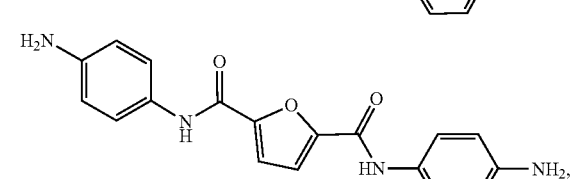
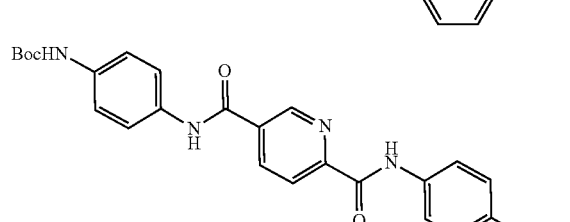
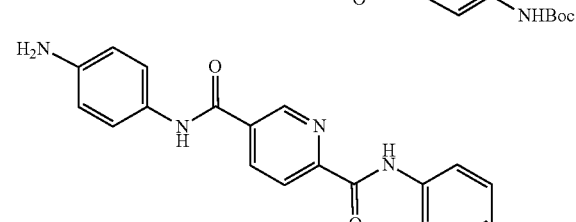
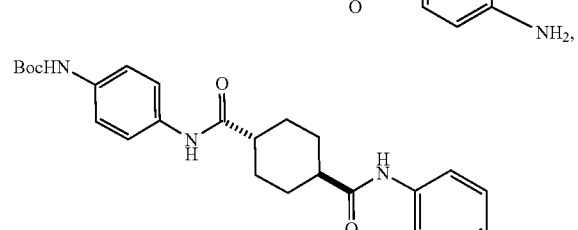
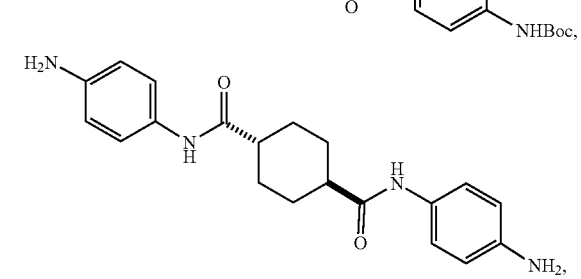
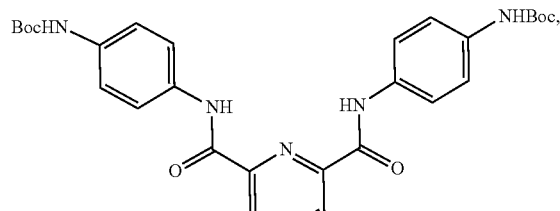
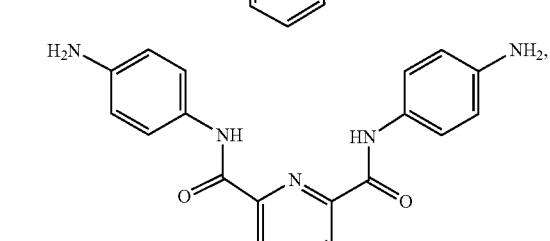
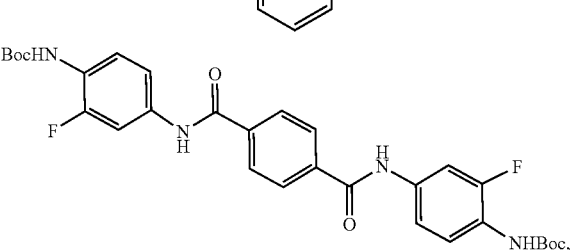
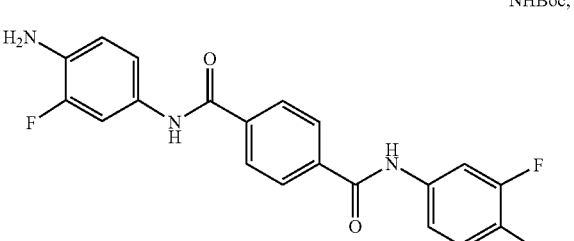
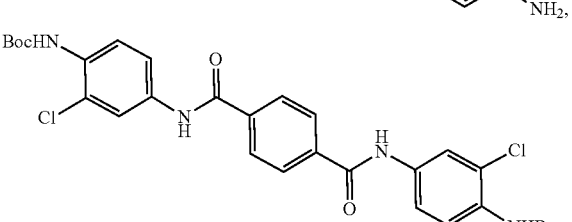
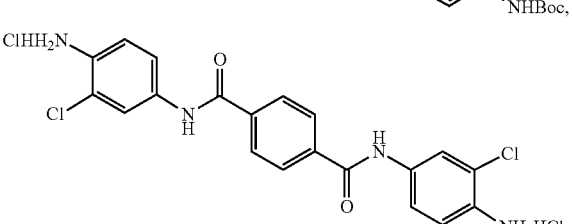
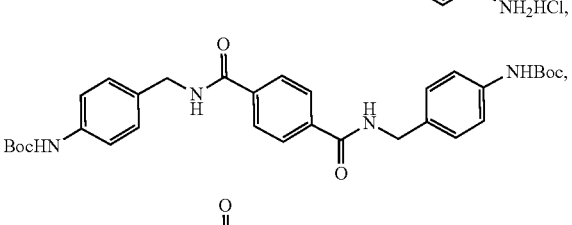

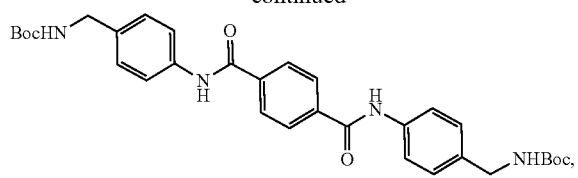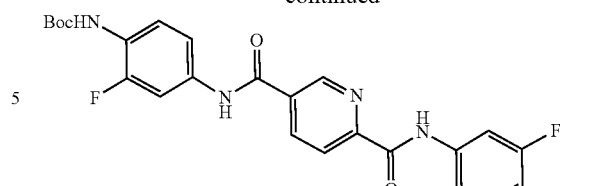

-continued
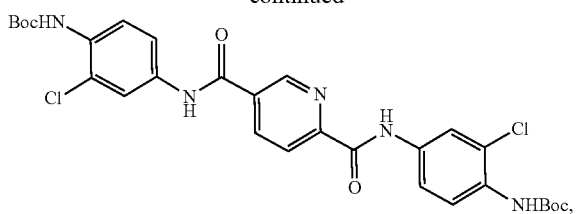
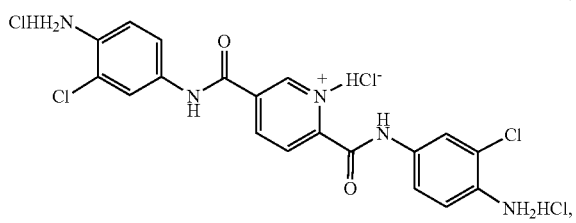
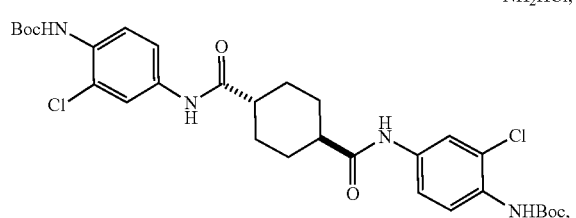
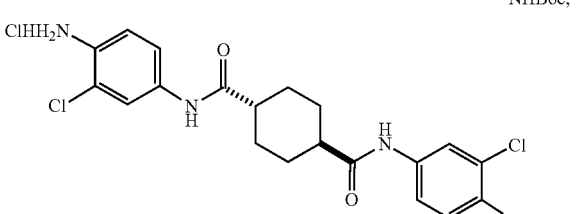
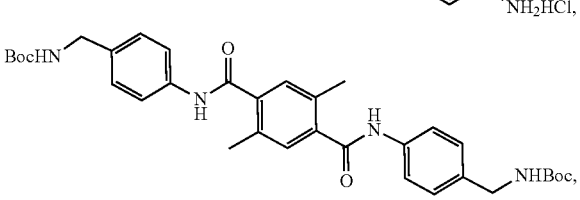
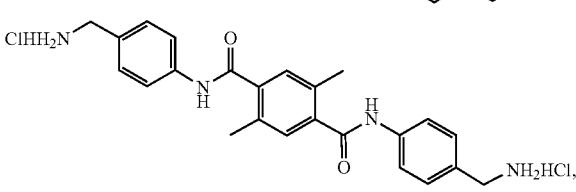
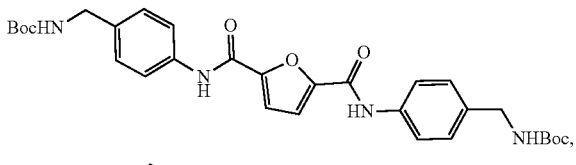
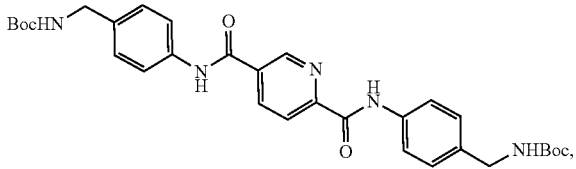
-continued
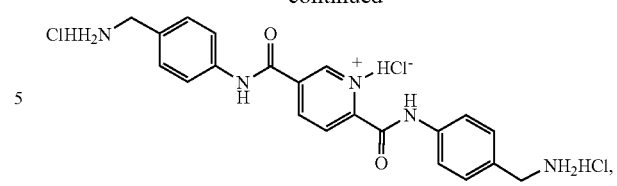
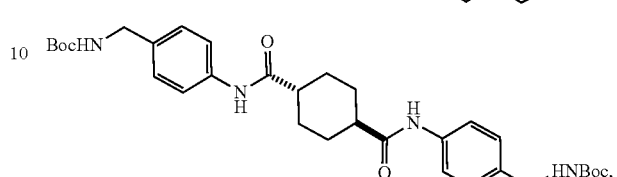
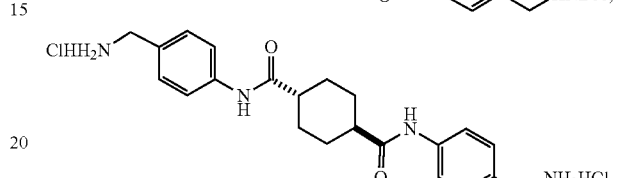
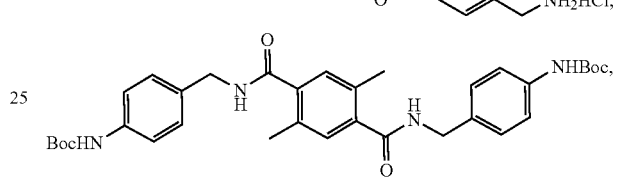
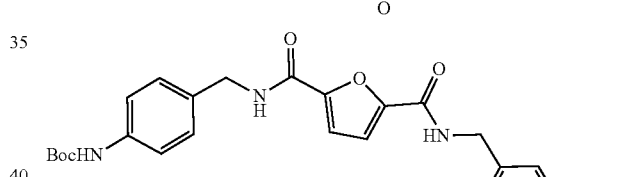
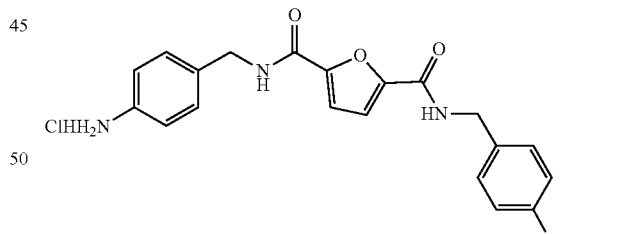
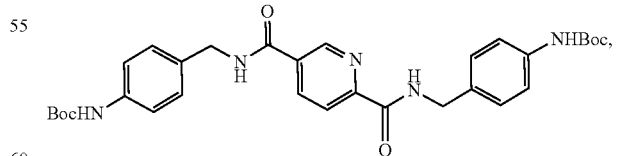
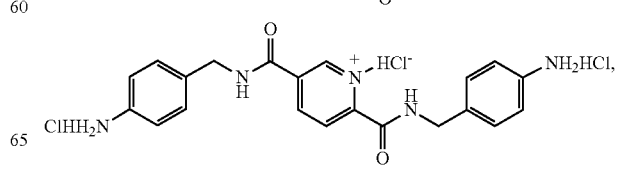

-continued
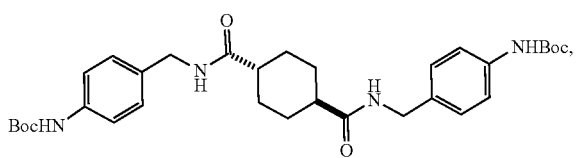
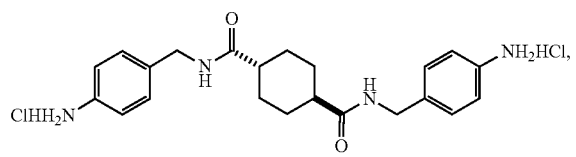
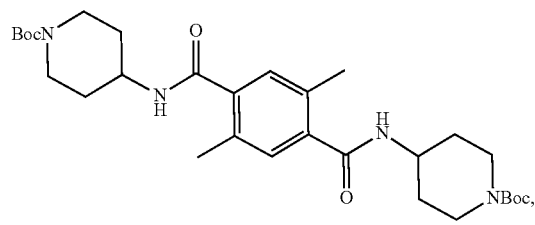
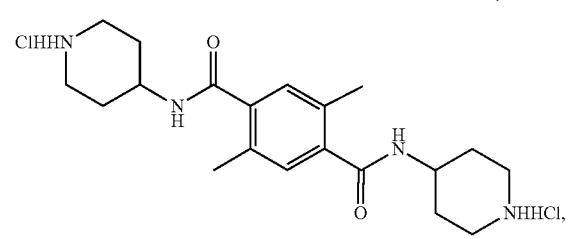
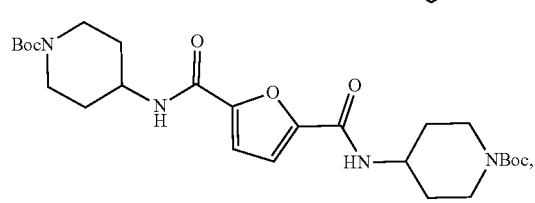
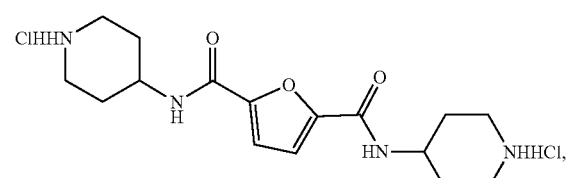
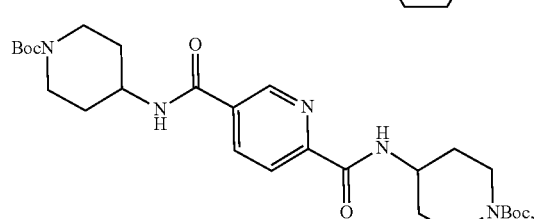
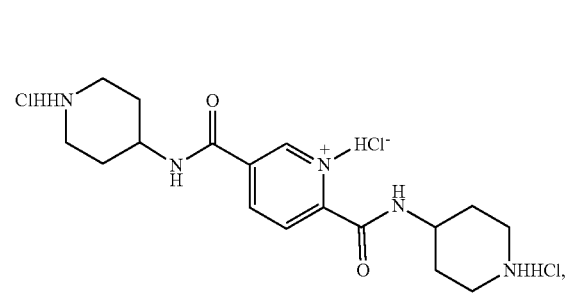
-continued
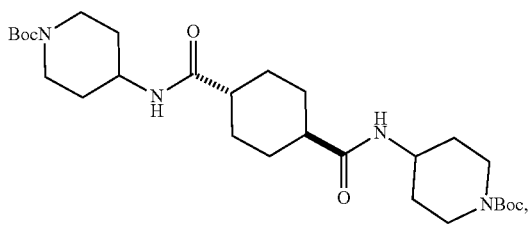
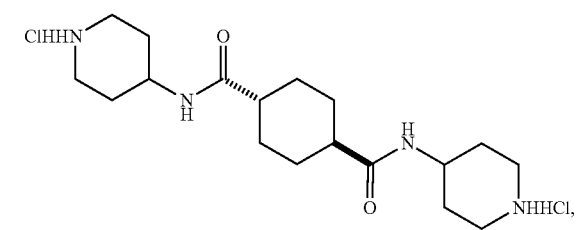
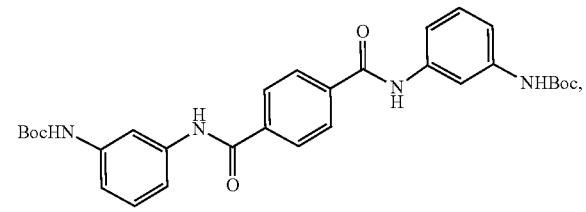
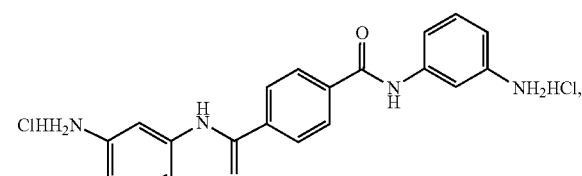
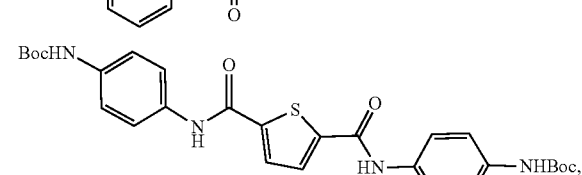
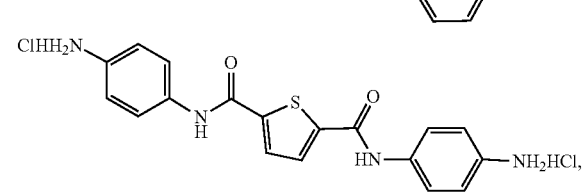
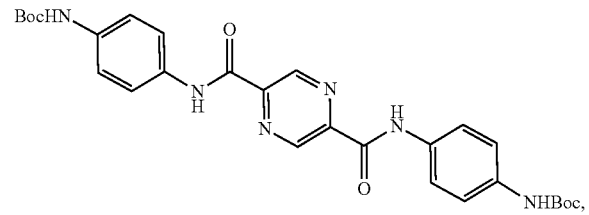
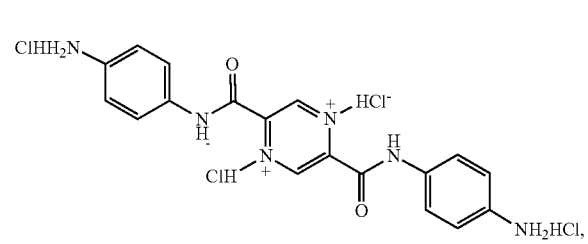

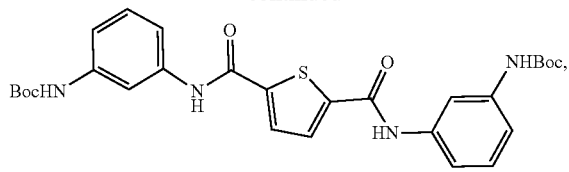

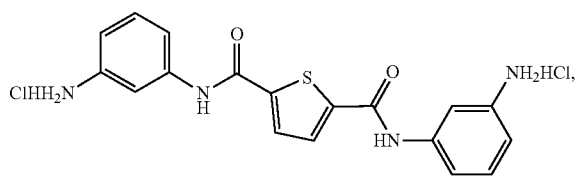

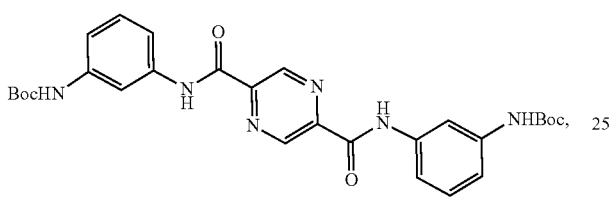

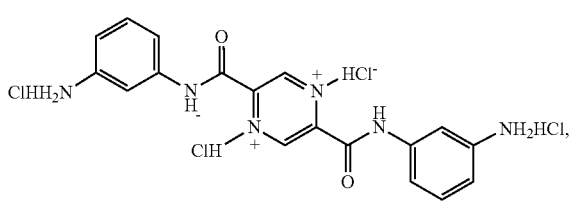

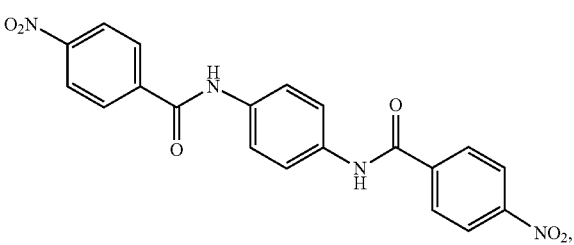

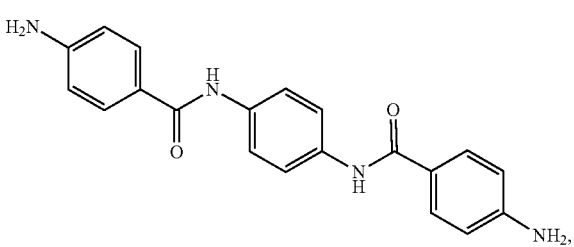

In some examples, the compounds disclosed herein can have a structure below:

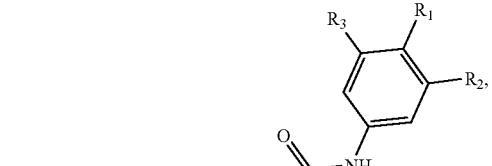

wherein $R_1$, $R_2$, and $R_3$ are as described herein.

In some examples, the compounds disclosed herein can have a structure below:

wherein $R_1$ is as described herein.

In some examples, the compounds disclosed herein can have a structure below:

In some examples, the compounds can have a structure represented in Table 1.

Methods for inhibiting WEE epigenetic activity are also disclosed. The method can include administering an effective amount of a compound described herein.

Methods for reducing the risk of, preventing, or treating cancer in a subject are also disclosed. The method can include administering to the subject an effective amount of a compound described herein. The cancer of the disclosed methods can be any cell in a subject undergoing unregulated growth, invasion, or metastasis. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer. In preferred embodiments, the cancer is non-small lung cancer or ovarian cancer.

In some embodiments, the cancer of the disclosed methods is a p53-deficient tumor cell. Inhibition of WEE1 activity prevents the phosphorylation of $CDCl_2$ and impairs the G2 DNA damage checkpoint. This can lead to apoptosis upon treatment with DNA damaging chemotherapeutic agents. Unlike normal cells, most p53-deficient or mutated human cancers lack the G1 checkpoint as p53 is the key regulator of the G1 checkpoint and these cells rely on the G2 checkpoint for DNA repair to damaged cells. Annulment of the G2 checkpoint may therefore make p53-deficient tumor cells more vulnerable to antineoplastic agents and enhance their cytotoxic effect.

As WEE1 inhibitors can act as a chemosensitizing agent for certain chemotherapeutic agents, in some embodiments, the method involves selecting a WEE1 inhibitor and a WEE1-sensitive antineoplastic drug, such as a DNA damaging chemotherapeutic agent.

Chemotherapy drugs can be divided into several groups based on factors such as how they work, their chemical structure, and their relationship to another drug. Because some drugs act in more than one way, they may belong to more than one group. Alkylating agents directly damage DNA to prevent the cancer cell from reproducing. Therefore, in some embodiments, the WEE1-sensitive or WEE1-insensitive chemotherapeutic agent is a DNA damaging chemotherapeutic agent. For example, in some embodiments, the DNA damaging chemotherapeutic agents is a platinum-based antineoplastic agent, such as carboplatin or cisplatin.

Antimetabolites are a class of drugs that interfere with DNA and RNA growth by substituting for the normal building blocks of RNA and DNA. Therefore, in some embodiments, the WEE1-sensitive or WEE1-insensitive chemotherapeutic agent is an antimetabolite chemotherapeutic agent, such as 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, or Thioguanine.

Anthracyclines are anti-tumor antibiotics that interfere with enzymes involved in DNA replication. Therefore, in some embodiments, the WEE1-sensitive or WEE1-insensitive chemotherapeutic agent is an anthracycline, such as Daunorubicin, Doxorubicin (Adriamycin®), Epirubicin, or Idarubicin. In some embodiments, the chemotherapeutic agent is a non-anthracycline anti-tumor antibiotics, such as Actinomycin-D, Bleomycin, or Mitomycin-C. In some embodiments, the chemotherapeutic agent is the anti-tumor antibiotic Mitoxantrone.

Topoisomerase inhibitors interfere with enzymes called topoisomerases, which help separate the strands of DNA so they can be copied. Therefore, in some embodiments, the WEE1-sensitive or WEE1-insensitive chemotherapeutic agent is a topoisomerase inhibitors, such as topotecan, or irinotecan (CPT-11), etoposide (VP-16), or teniposide.

Mitotic inhibitors are often plant alkaloids and other compounds derived from natural products. They can stop mitosis or inhibit enzymes from making proteins needed for cell reproduction. Therefore, in some embodiments, the WEE1-sensitive or WEE1-insensitive chemotherapeutic agent is a mitotic inhibitor, such as paclitaxel (Taxol®), docetaxel (Taxotere®), ixabepilone (Ixempra®), vinblastine (Velban®), vincristine (Oncovin®), vinorelbine (Navelbine®), or Estramustine (Emcyt®).

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publiation No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VEL- CADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

Example 1: A Novel Allosteric Inhibitor of WEE1 Kinase

ABSTRACT: WEE1, a nuclear tyrosine kinase has shown to be an indispensable regulator of cell cycle. It phosphorylates Cdk1 (Cyclin-dependent kinase 1) at the amino acids Tyr15 and Thr14, inhibiting kinase activity of Cdk1 and prevents entry into mitosis until DNA replication has been completed. Role of WEE1 in coordinating transition between DNA replication and mitosis was further accentuated upon recent discovery of its role as a global histone synthesis regulator. WEE1 phosphorylated histone H2B at tyrosine 37 (pY37-H2B) in a distinct spatiotemporal manner and these epigenetic marks were deposited upstream of the histone gene cluster leading to global suppression of histone transcription in late S phase, prior to its entry into G2/M phase. Although, a dual function of WEE1 kinase, a mitotic gatekeeper and a surveyor of chromatin synthesis reveal a new cancer therapeutic option, an inhibitor that specifically overcomes WEE1 epigenetic activity. Indeed, many malignancies including glioblastoma (GBM), melanoma, prostate and triple negative breast cancers exhibit elevated WEE1 expression. Herein is described a new class of allosteric inhibitor, WEIN-159 (WEE1 Epigenetic Inhibitor #159) that overcomes interaction between WEE1 and SIRT7 histone deacetylase, leading to significant increase in H3K18, H3K12 and H3K5 acetylation in the promoters of tumor suppressors. Restoration of H3K18-acetylation upon WEIN-159 treatment not only reinstated expression of tumor suppressors but also suppressed prostate tumor growth, revealing a new therapeutic modality for difficult to treat malignancies.

INTRODUCTION: WEE1 is an evolutionarily conserved nuclear tyrosine kinase that is markedly active during the S/G2 phase of the cell cycle. It was first discovered 25 years ago as a cell division cycle (cdc) mutant-wee1-in the fission yeast, *Schizosaccharomyces pombe*. Fission yeast lacking WEE1 are characterized by a smaller cell size, and this phenotype has been attributed to the ability of WEE1 to negatively regulate the activity of cyclin dependent kinase, Cdc2 (Cdc28 in budding yeast and CDK1 in human), in the Cdc2/CyclinB complex.

A dual role for WEE1 in S phase regulation and histone synthesis: Chromatin integrity—the synthesis and packaging of the nascent DNA with histones—is critical for proper chromosome condensation, segregation, epigenetic inheritance, and genome stability. Eukaryotic cells tightly regulate synthesis of core chromatin components, during each cell cycle. Although processes that interfere with DNA replication compromise genetic integrity, alterations in histone stoichiometry or mutations in histone genes are linked to chromosome loss, altered chromatin architecture, and cancer. All eukaryotic cells maintain a precise ratio of core histones to the newly synthesized DNA; both higher and lower ratios of histones to the DNA have deleterious effects. In addition, transcription of histones is tightly regulated and coordinated with the cell cycle.

Just as histone synthesis is exquisitely regulated during the cell cycle, its termination is also precisely synchronized with cell cycle progression. Higher eukaryotes have multiple copies of histone genes for the core histones, each encoding a fraction of the total histone protein to deal with the large-scale histone synthesis required for packaging newly synthesized DNA into chromatin during S-phase. These genes are organized in three major clusters in humans, HIST1 (55 histone genes), HIST2 (6 histone genes), and HIST3 (3 histone genes), with copies being arranged in tandem. At the end of S-phase or upon replication inhibition, histone levels are rapidly lowered. Recently, a new function-WEE1 was identified and shown to directly phosphorylate the mammalian core histone H2B at tyrosine 37 in a cell cycle dependent manner Nucleosomes upstream of the mouse histone gene cluster I (HistI) were found to be decorated by epigenetic marks-histone H2B tyrosine phosphorylation at 37 residue (pY37-H2B) precisely at the end of S-phase when DNA synthesis is completed.

Collectively, these data suggest a role for WEE1 as a 'chromatin synthesis sensor' by two sequential phosphorylation events: (i) Y15-phosphorylation of CDK1 throughout S phase to prevent exit from S phase until DNA replication is completed, and (ii) Y37-phosphorylation of H2B at the end of S phase to terminate histone synthesis, thus maintaining the right histone-DNA stoichiometry prior to mitotic entry.

Epigenetic marks manifested during the cell cycle: In addition to pY37-H2B, a number of other histone marks are regulated in a cell-cycle dependent manner Methylation of histone H3 (K4me3, K9me1, K9me2) and H4 (K20me1) and acetylation of H4 (K5, K16 and K56) are also regulated in cell cycle dependent manner. Although H4K5 acetylation marks are critical for deposition of nascent histones during chromatin assembly by histone chaperones during S phase; they are likewise erased after nucleosome assembly to restore the chromatin structure. The histone deacetylases, HDAC1, HDAC2, or HDAC3, remove H4K5 acetyl marks and their recruitment to newly synthesized DNA is a regulated process. It has been shown that WEE1 interacts with HIRA protein [14] and Chicken HIRA has been shown to interact with HDAC1 and 2 [22]. Whether recruitment of HIRA by pY37-H2B establishes a binding platform for the further recruitment of HDACs to deacetylate H4K5, H3K18, H3K12 and H3K9 acetylation in the chromatin remains to be established.

WEE1 and its role in cancer: The central role of WEE1 in integrating various aspects of cell cycle progression, histone synthesis, and genomic stability makes it an important target for cancer treatment. Gene expression profiling of various tumors revealed that the WEE1 kinase is overexpressed in hepatocellular carcinoma (HCC), Glioblastoma multiforme (GBM), luminal, and triple negative breast cancers (TNBC) as well as malignant melanomas. In addition, pharmacologic inhibition by WEE1 inhibitor II or molecular knockdown of WEE1 sensitized PC3 neuroendocrine prostate cancer cells to an Hsp90 inhibitor. Further, WEE1 inhibition by WEE1 inhibitor II, at micromolar concentrations as monotherapy, reduced cell viability, increased DNA damage, and induced apoptosis in various breast cancer cells that represent estrogen-receptor positive, HER-amplified, and triple-negative subtypes, but not in normal mammary epithelial cells and fibroblasts.

Need for WEE1 epigenetic inhibitor: WEE1 overexpression and the resultant decrease in histone levels could lead to inefficient chromatin packaging, making the DNA more accessible to the DNA damage repair machinery and promoting radioresistance. The ability of WEE1 to downregulate histone levels could explain why cancer cells become dependent on its epigenetic activity. In addition to acquiring radioresistance, decreased nucleosomal packaging and consequently local alterations in chromatin architecture may activate transcription of pro-proliferative genes or even oncogenes that are otherwise kept in check in normal cells. Overexpression of WEE1 in cancer types could be exploited by using WEE1-specific small molecule inhibitors. One such inhibitor MK-1775 is in clinical trials.

The aim of this example was to develop an epigenetic inhibitor of WEE1 that would increase histone dosage in actively replicating cancer cells, significantly compromising their proliferation. Further, when combined with DNA damaging agents, would interfere with the DNA repair machinery and compromise genome integrity. Consistent with this hypothesis, it is expected that the WEE1 epigenetic inhibitor be able to radiosensitize human lung, breast, skin, brain, and prostate cancer cells to DNA damaging agents, and expect to synergize with CHK1 inhibitors to induce cytotoxicity. Moreover, cancer cells treated with hydroxyl urea (which inhibits DNA synthesis) and WEE1 epigenetic inhibitors are expected to contain a marked increase in disorganized mitotic spindles and abnormal mitoses.

Enzymes that promote or reverse histone modifications have emerged as major targets for the development of small molecule inhibitors, commonly referred as epigenetic inhibitors. Many of these are already in different stages of clinical trials with significant success in hematologic cancers. The precision with which histone modifying enzymes modify a specific amino acid residue in a histone makes them ideal candidates for drug discovery efforts, however, because of a highly heterogeneous nature of disease, the efficacy of the epigenetic inhibitor is likely to be seen in a subset of cancer patients that are addicted to the activity of the histone modifying enzyme, making them highly specific. This and other early successes, suggest that WEE1 epigenetic inhibition may be a useful strategy for treatment of certain cancers, however such inhibitor is not yet reported. Herein is reported the discovery and detail characterization of WEE1 epigenetic inhibitor, believed to be a first of its kind.

Results

Designing of a Novel inhibitor Screening Platform: To identify a WEE1 epigenetic inhibitor, a novel ELISA based assay wherein biotinylated peptide derived from H2B spanning Tyr37 site were immobilized on streptavidin plate was considered. A full length human WEE1 kinase that was enzymatically active was purified from insect cell. Purified WEE1 kinase was added with (or without) compounds and the phosphorylation of H2B-peptide was detected using Tyr-specific antibodies, that were conjugated to HRP (horse radish peroxidase enzyme). The substrate was detected by spectrophotometer, which corresponds to degree of WEE1 mediated phosphorylate histone H2b. NCI diversity set compound library (~1600 compounds) was used for the screening. A known WEE1 kinase inhibitor, AZD-1775 (also known as MK-1775) that inhibits WEE1 ability to suppress both, Cdc2-Y15 and H2B-Y37 phosphorylations, was used as a positive control.

Figure 2A:
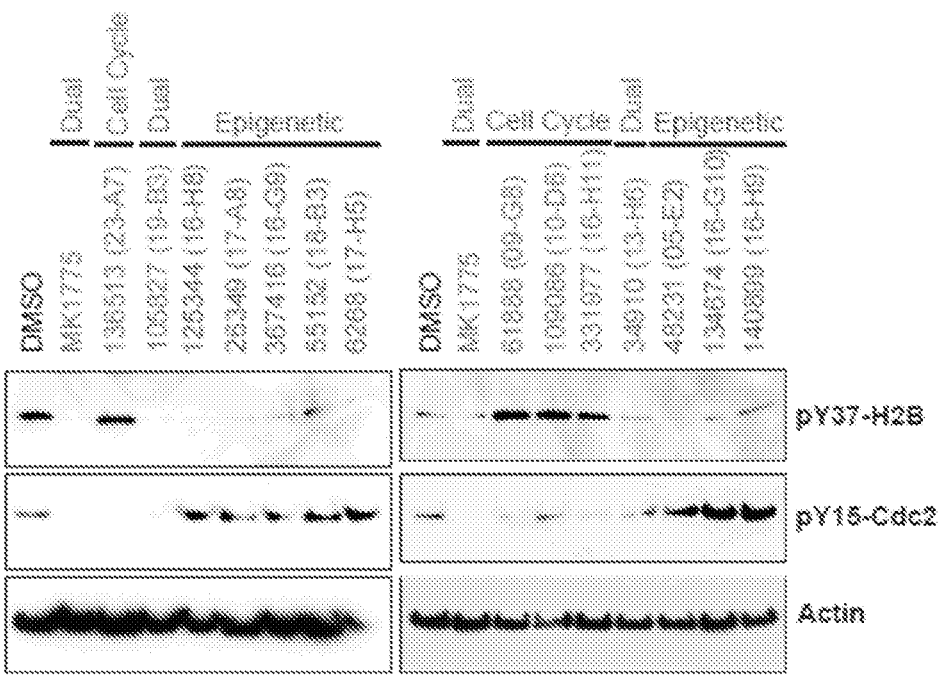
FIGS. 2A-2B show identification of 3 distinct types of inhibitors.

Identification of compounds with WEE1 epigenetic inhibitory role: 14 'hits' that were identified in the screen are shown in FIG. 1. These compounds were further tested for their ability to inhibit WEE1 epigenetic activity. Prostate cancer derived LNCaP cells were treated with 3 uM of compounds for 48 hours. Cells were harvested, lysates were prepared, and WEE1 epigenetic activity was detected by determining histone H2B Tyr37-phopshorylation (pY37-H2B). Lysates were also assessed for WEE1 cell cycle inhibitory activity by determining Cdc2 Tyr15-phosphorylation (pY15-Cdc2). AZD-1775 which potently inhibits its kinase activity and thus acts as a 'dual' inhibitor exhibited loss of both H2B and Cdc2-phosphorylation, in contrast compounds 136513 (23-A7), 61888 (09-G8), 109086 (10-D6) and 331977 (16-H11) exhibited robust inhibition of Cdc2 Tyr15-phosphorylation, but had no effect on H2B Tyr37-phosphotylation (FIG. 2A). These are named as 'Cell Cycle' inhibitors. Also identified were 8 compounds, 125344 (16-H8), 26349 (17-A8), 367416 (16-G9), 55152 (18-B3), 6268 (17-H5), 48231 (05-E2), 134674 (16-G10) and 140899 (16-H9), that specifically suppressed H2B Tyr37-phosphotylation but did not affect Cdc2 Tyr15-phosphorylation (FIG. 2A). These compounds are the 'Epigenetic' inhibitors. Further identified were 2 dual inhibitors, 105827 (19-B3) and 34910 (13-H6) which suppressed both Cdc2 Tyr15- and H2B Tyr37-phosphotylation.

Figure 2B:
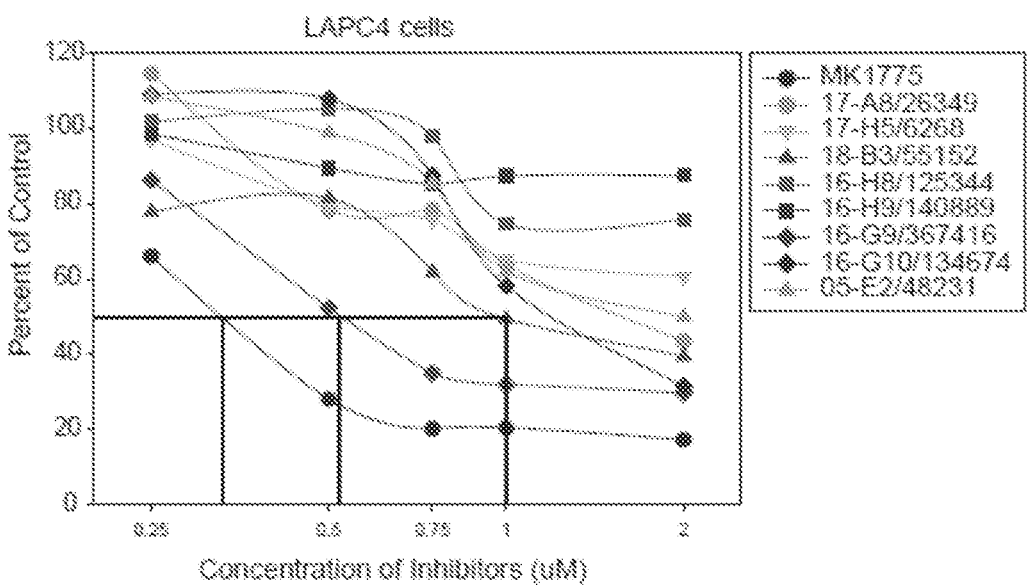

7 of these epigenetic inhibitors in various assays such as cell proliferation assay, an in vitro kinase assay were performed and WEE1 autophosphorylation in vivo was determined. Prostate cancer derived LAPC4 cells were treated with inhibitors and its effect on cell proliferation was examined. Compounds 367416 (16-G9) and 55152 (18-B3) significantly compromised cell proliferation, with $IC_{50}$ of 0.5 µM and 1 µM, respectively (FIG. 2B). As a control AZD1775 was used with $IC_{50}$ of 0.35 µM.

Figures 3A, 3B, 3C:
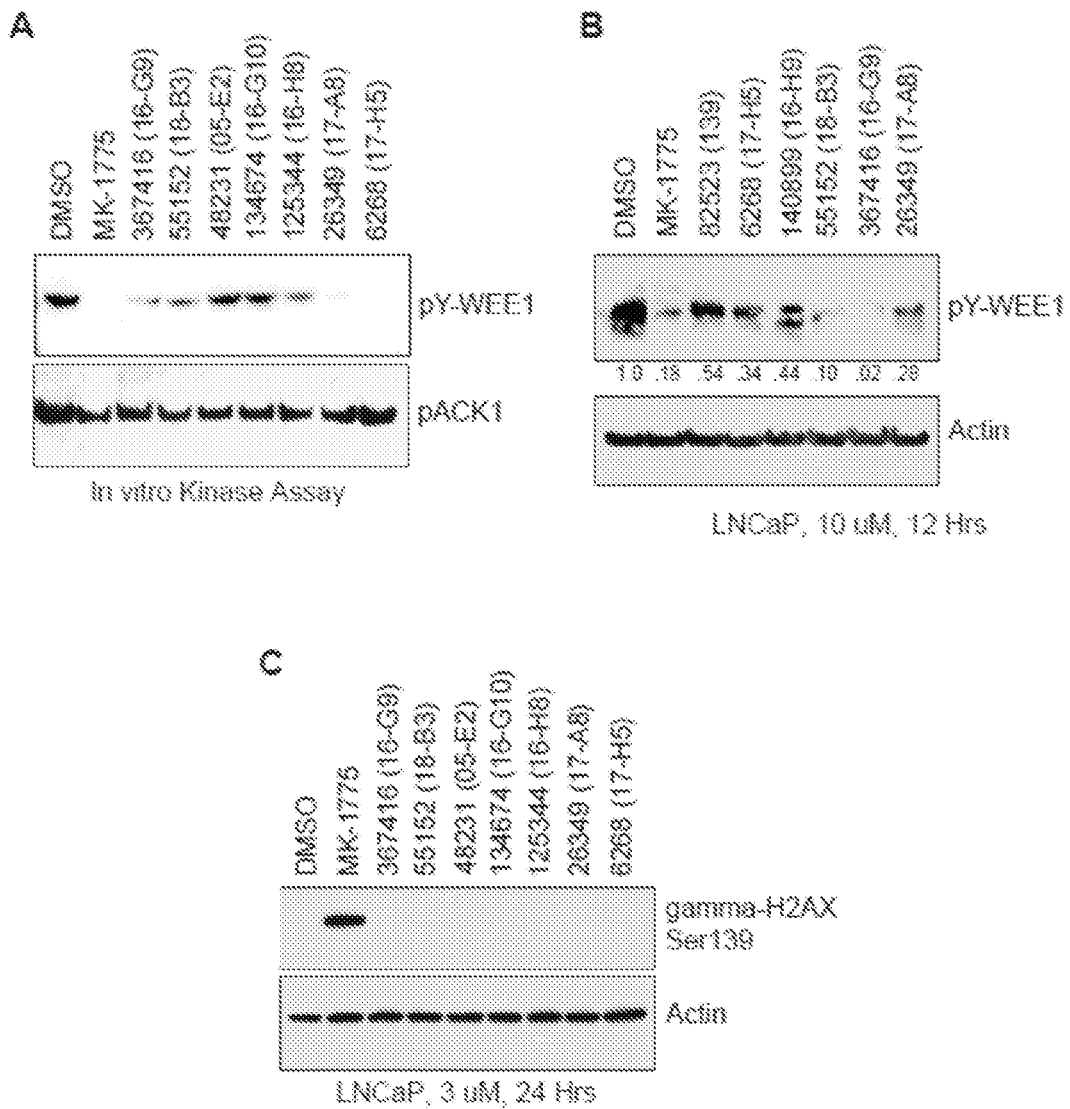
FIGS. 3A-3C shows structures of 'hits' identified in WEE1 epigenetic inhibitor screen.

To determine direct binding of these compounds causing WEE1 inhibition, a full length WEE1 kinase protein was incubated with the compounds. The reaction mix was immunoblotted with pTyr-antibodies which revealed that compounds 367416 (16-G9), 55152 (18-B3), 26349 (17-$A_8$) and 6268 (17-H5) exhibited significant loss of WEE1 kinase activity (FIG. 3A). As a control, purified ACK1 kinase was also incubated with these compounds, none of these compounds were able to inhibit ACK1 kinase activity. These inhibitors were further validated by assessing their ability to suppress endogenous WEEE activity; LNCaP cells were treated with 10 µM of these compounds overnight. WEE was immunoprecipitated followed by immunoblotting with pTyr-antibodies revealed significant loss of WEE1 autophosphorylation upon 367416 (16-G9) and 55152 (18-B3) treatment (FIG. 3B). Taken together, these data indicated that 367416 (16-G9) and 55152 (18-B3) are two potent WEE1 inhibitors in vivo.

H2AX becomes phosphorylated on serine 139, called gamma-H2AX, is a marker of DNA damage as it localizes to sites of DNA strand breaks. This sensor then functions to trigger activation of the DNA damage response pathways. To assess whether any of the epigenetic inhibitors are potent DNA-damaging agents, cells were treated with the compounds followed by immunoblotting with gamma-H2AX antibodies. None of the compounds were able to cause DNA damage, however, AZD-1775 a positive control, suppressed WEE1 pathway leading to abrogation of G2-arrest and intensified double-strand DNA breakage (seen as gamma-H2AX) following drug exposure (FIG. 3C).

Figures 4A, 4B:
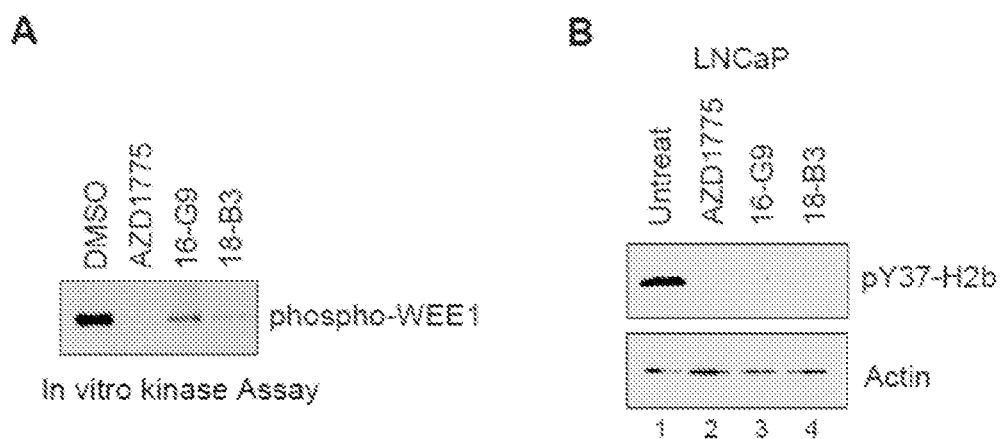
FIGS. 4A-4B show structures of 'hits' identified in WEE1 epigenetic inhibitor screen.
Figures 5A, 5B, 5C:
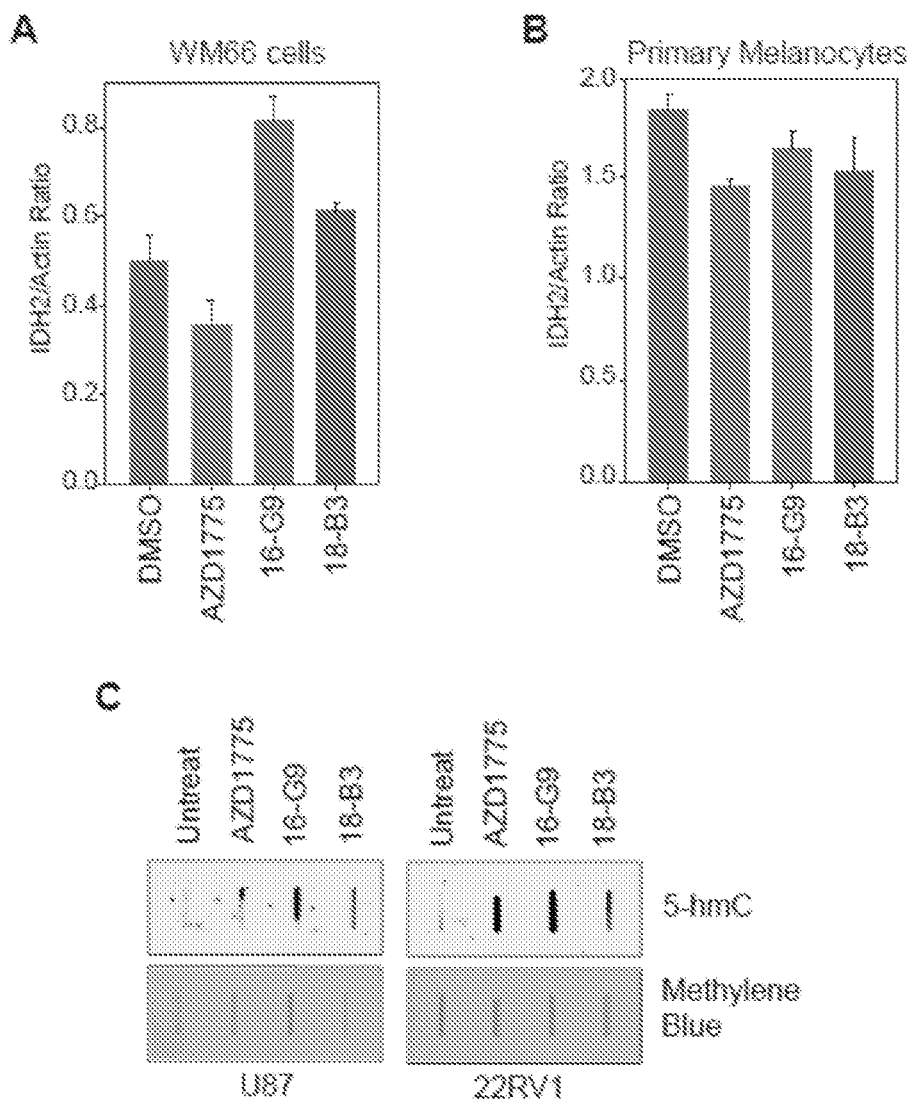
FIGS. 5A-5C show inhibition of WEE1 epigenetic activity lead to increased IDH2 and 5-hmC expression. WM66 cells (FIG. 5A) or primary melanocytes (FIG. 5B) were treated with vehicle or compounds (10 uM) for 16 hr. Total RNA was isolated followed by qRT-PCR with IDH2 and actin primers.
Figure 6:
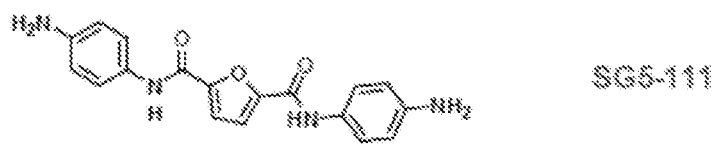
FIG. 6 shows libraries around NSC55152 (18-B3). The libraries were prepared around NSC55152 (18-B3). See the details of synthesis in FIGS. 17 and 18.
Figure 6:
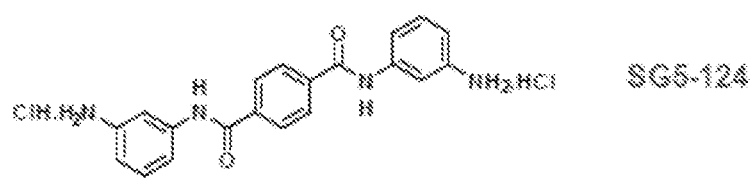
Figure 6:
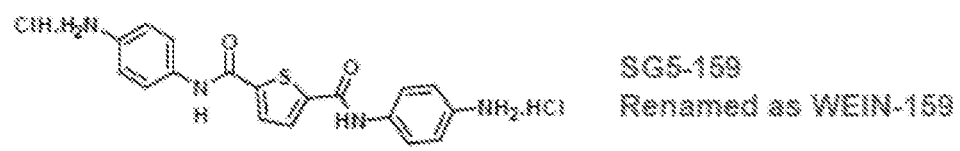
Figure 6:
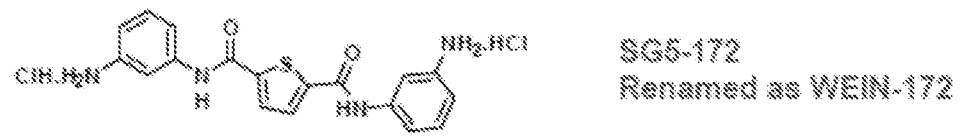

Identification of 55152 (18-B3) scaffold as a WEE1 epigenetic inhibitor: Two major hits, 367416 (16-G9) and 55152 (18-B3) were taken up for further characterization. An in vitro kinase assay using full length WEE1 kinase revealed that 18-B3 suppresses kinase activation better than 16-G9 (FIG. 4A). It was also reflected in complete loss of H2B Tyr37-phosphorylation in LNCaP cells (FIG. 4B). Earlier it was demonstrated that WEE1 deposits pY37-H2B repressive marks in IDH2 gene suppressing its expression, resulting in up-regulating 5hmC levels. Accordingly, melanoma cell line WM66 and primary melanocytes were treated with inhibitors and IDH2 mRNA levels were measure by real time PCR. Significant increase in IDH2 mRNA levels was seen upon 16-G9 and 18-B3 treatments in WM66 cells, but not in primary melanocytes (FIG. 5A). Corresponding increase in 5hmC levels were also noticed (FIG. 5B).

Derivatization of 55152 (18-B3) scaffold: generation of compounds: Various derivatives of 55152 (18-B3) scaffold were generated, shown in Table 1.

TABLE 1

| Name<br>Molecular Wt (Amt. Supplied mg) | ELISA Inhibition (%) |
|---|---|
| SG5-061 (55152 in-house) M.W. = 346 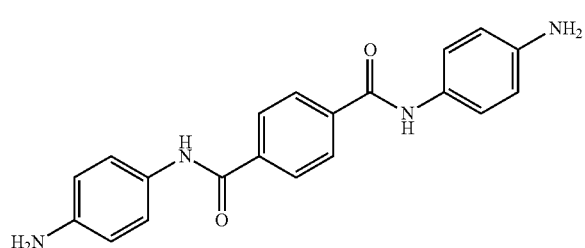 | 112, 81, 82, 87, 83, 100, 106 |
| SG5-099 M.W. = 546.62 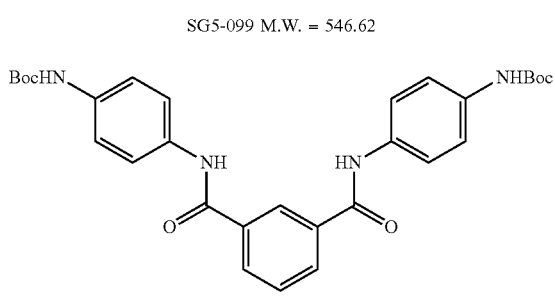 | −14 |

TABLE 1-continued

| Name<br>Molecular Wt (Amt. Supplied mg) | ELISA<br>Inhibition<br>(%) |
| --- | --- |
| SG5-103 M.W. = 346.39 | 12 |
| SG5-106 M.W. = 574.68 | −23 |
| SG5-110 M.W. = 374.44 | 14 |
| SG5-107 M.W. = 536.59 | −8 |
| SG5-111 M.W. = 336.35 | 46, 55 |

TABLE 1-continued

| Name<br>Molecular Wt (Amt. Supplied mg) | ELISA<br>Inhibition<br>(%) |
|---|---|
| SG5-119 M.W. = 547.61 | −17 |
| SG5-124 M.W. = 347.38 | 73, 103 |
| SG5-121 M.W. = 552.67 | −7 |
| SG5-126 M.W. = 352.44 | −39 |
| SG5-123 M.W. = 547.61 | −39 |

TABLE 1-continued

| Name<br>Molecular Wt (Amt. Supplied mg) | ELISA Inhibition (%) |
|---|---|
| SG5-128 M.W. = 347.38 | 2 |
| SG5-133-1 M.W. = 582.60 | −57 |
| SG5-137-1 M.W. = 382.37 | −24 |
| SG5-133-2 M.W. = 615.51 | −38 |
| SG5-137-2 M.W. = 488.19 | −52 |

TABLE 1-continued

| Name<br>Molecular Wt (Amt. Supplied mg) | ELISA Inhibition (%) |
|---|---|
| SG5-133-3 M.W. = 574.68 | −17, 50 |
| SG5-137-3 M.W. = 447.36 | 32, 60 |
| SG5-133-4 M.W. = 574.68 | −26, 28 |
| SG5-137-4 M.W. = 447.36 | −17, 21 |
| SG5-133-5 M.W. = 530.67 | −42, 39 |
| SG5-137-5 M.W. = 403.35 | −40, 46 |

TABLE 1-continued

| Name<br>Molecular Wt (Amt. Supplied mg) | ELISA Inhibition (%) |
|---|---|
| SG5-140-1 M.W. = 610.66 | 25 |
| SG5-147-1 M.W. = 483.34 | 41 |
| SG5-140-2 M.W. = 572.57 | 25 |
| SG5-147-2 M.W. = 445.25 | 37 |
| SG5-140-3 M.W. = 583.59 | 22 |
| SG5-147-3 M.W. = 492.73 | 50 |

TABLE 1-continued

| Name<br>Molecular Wt (Amt. Supplied mg) | ELISA<br>Inhibition<br>(%) |
| --- | --- |
| SG5-140-4 M.W. = 588.65 | 20 |
| SG5-147-4 M.E. = 461.33 | 20 |
| SG5-140-5 M.W. = 643.56 | 24 |
| SG5-147-5 M.W. = 516.24 | 2 |
| SG5-140-6 M.W. = 605.47 | 17 |

TABLE 1-continued

| Name<br>Molecular Wt (Amt. Supplied mg) | ELISA<br>Inhibition<br>(%) |
|---|---|
| SG5-147-6 M.W. = 478.15 | 13 |
| SG5-140-7 M.W. = 616.50 | 12 |
| SG5-147-7 M.W. = 525.64 | 9 |
| SG5-140-8 M.W. = 621.56 | 25 |
| SG5-147-8 M.W. = 494.24 | 17 |

TABLE 1-continued
| Name<br>Molecular Wt (Amt. Supplied mg) | ELISA<br>Inhibition<br>(%) |
|---|---|
| SG5-140-9 M.W. = 602.73 | 18 |
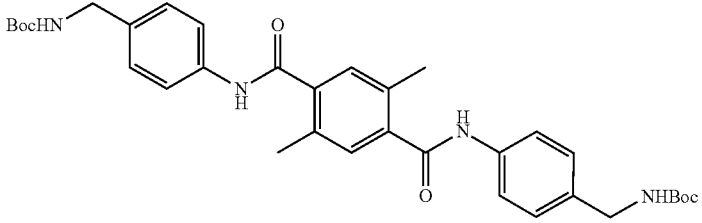 [SMILES: Cc1cc(C(=O)Nc2ccc(CNC(=O)OC(C)(C)C)cc2)c(C)cc1C(=O)Nc1ccc(CNC(=O)OC(C)(C)C)cc1]
| SG5-147-9 M.W. = 475.41 | 9 |
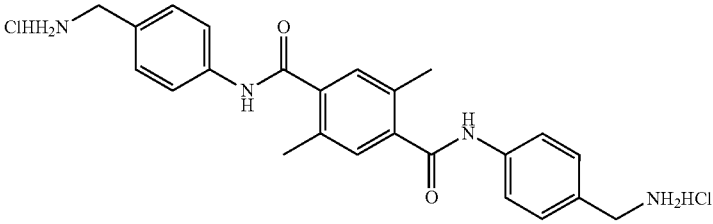
| SG5-140-10 M.W. = 564.64 | 13 |
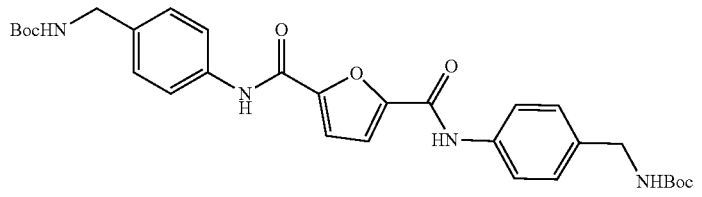 [SMILES: CC(C)(C)OC(=O)NCc1ccc(NC(=O)c2ccc(C(=O)Nc3ccc(CNC(=O)OC(C)(C)C)cc3)o2)cc1]
| SG5-147-10 M.W. = 437.32 | 4 |
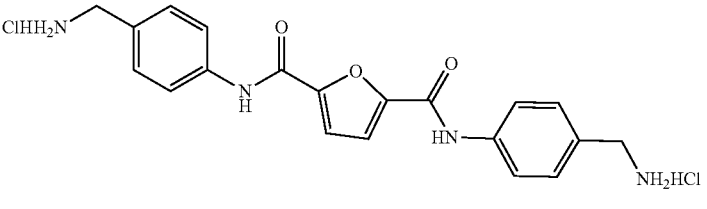
| SG5-140-11 M.W. = 575.67 | −6 |
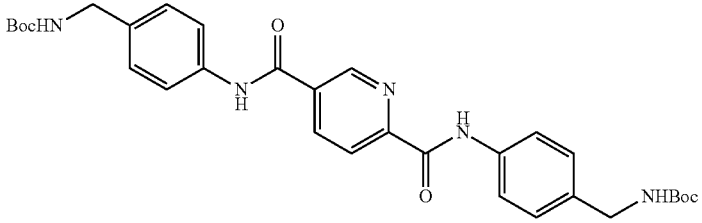 [SMILES: CC(C)(C)OC(=O)NCc1ccc(NC(=O)c2ccc(C(=O)Nc3ccc(CNC(=O)OC(C)(C)C)cc3)nc2)cc1]

TABLE 1-continued

| Name<br>Molecular Wt (Amt. Supplied mg) | ELISA<br>Inhibition<br>(%) |
| --- | --- |
| SG5-147-11 M.W. = 484.81 | 68 |
| SG5-140-12 M.W. = 580.73 | 4 |
| SG5-147-12 M.W. = 453.41 | −9 |
| SG5-140-13 M.W. = 602.73 | −4 |
| SG5-147-13 M.W. = 475.41 | 12 |

TABLE 1-continued

| Name<br>Molecular Wt (Amt. Supplied mg) | ELISA<br>Inhibition<br>(%) |
| --- | --- |
| SG5-140-14 M.W. = 564.64 | −4 |
| SG5-147-14 M.W. = 437.32 | −16 |
| SG5-140-15 M.W. = 575.67 | 12 |
| SG5-147-15 M.W. = 484.81 | 17 |
| SG5-140-16 M.W. = 580.73 | 8 |

TABLE 1-continued

| Name<br>Molecular Wt (Amt. Supplied mg) | ELISA<br>Inhibition<br>(%) |
|---|---|
| SG5-147-16 M.W. = 453.41 | −14 |
| SG5-140-17 M.W. = 558.72 | 10 |
| SG5-147-17 M.W. = 431.40 | 21 |
| SG5-140-18 M.W. = 520.63 | −27 |
| SG5-147-18 M.W. = 393.31 | −5 |
| SG5-140-19 M.W. = 531.65 | 28 |

TABLE 1-continued
| Name<br>Molecular Wt (Amt. Supplied mg) | ELISA<br>Inhibition<br>(%) |
| --- | --- |
| SG5-147-19 M.W. = 440.79 | 24 |
| 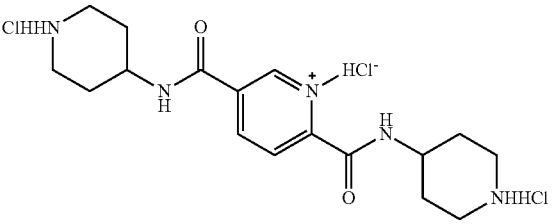 | |
| SG5-140-20 M.W. = 536.71 | 28 |
| 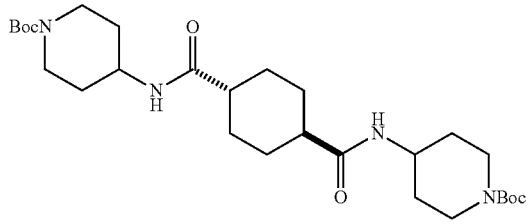 | |
| SG5-147-20 M.W. = 409.40 | 22 |
| 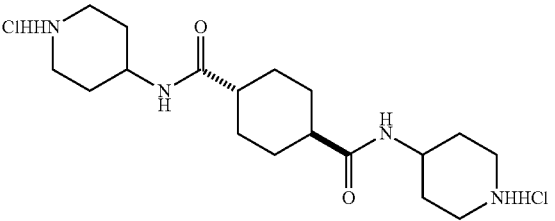 | |
SG5-153 M.W. = 546.62
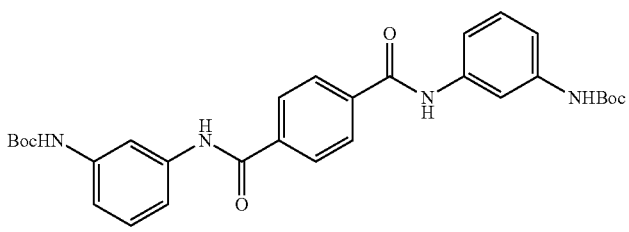 [SMILES: CC(C)(C)OC(=O)Nc1cccc(NC(=O)c2ccc(C(=O)Nc3cccc(NC(=O)OC(C)(C)C)c3)cc2)c1]
SG5-157 M.W. = 552.65
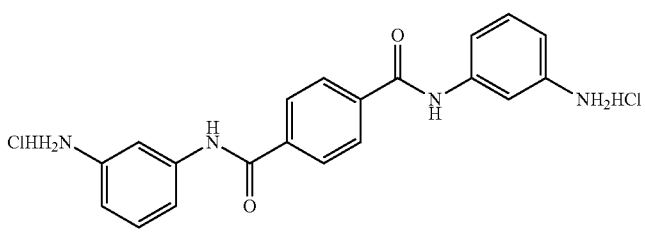

TABLE 1-continued
| Name<br>Molecular Wt (Amt. Supplied mg) | ELISA<br>Inhibition<br>(%) |
|---|---|
SG5-157 M.W. = 552.65
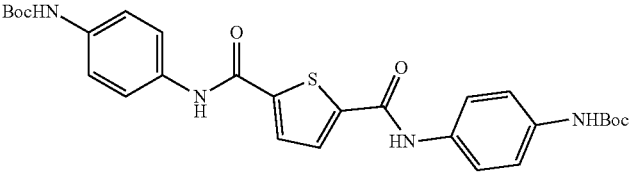 [SMILES: CC(C)(C)OC(=O)Nc1ccc(NC(=O)c2ccc(C(=O)Nc3ccc(NC(=O)OC(C)(C)C)cc3)s2)cc1]
SG5-159 M.W. = 45.33
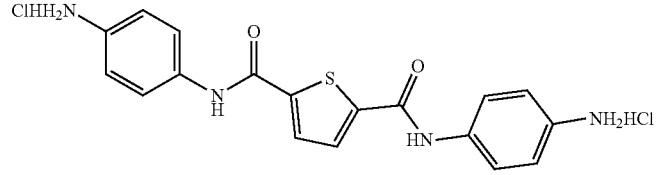
Renamed as WEIN-159
SG5-158 M.W. = 548.60
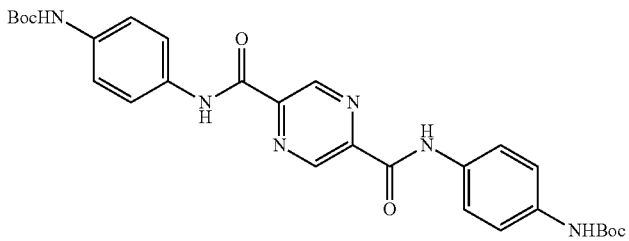 [SMILES: CC(C)(C)OC(=O)Nc1ccc(NC(=O)c2cnc(C(=O)Nc3ccc(NC(=O)OC(C)(C)C)cc3)cn2)cc1]
SG5-160 M.W. = 494.20
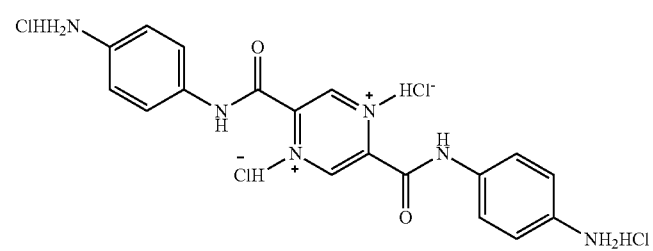
SG5-170 M.W. = 552.65
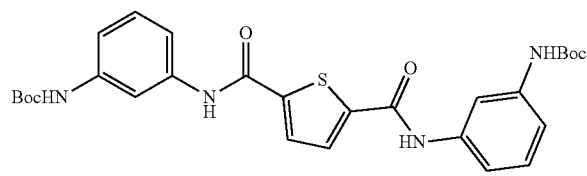 [SMILES: CC(C)(C)OC(=O)Nc1cccc(NC(=O)c2ccc(C(=O)Nc3cccc(NC(=O)OC(C)(C)C)c3)s2)c1]
SG5-172 M.W. = 425.33
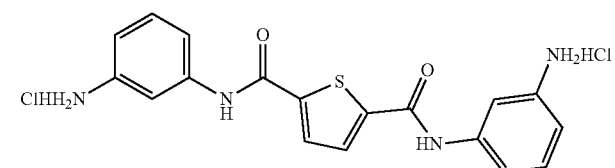

TABLE 1-continued

| Name Molecular Wt (Amt. Supplied mg) | ELISA Inhibition (%) |
|---|---|

SG5-171 M.W. = 548.60

SG5-173 M.W. = 494.20

SG5-161 (121836 in-house) M.W. = 406.35

SG5-162 M.W. = 346.39

ADME studies with 55152 (18-B3) and 367416 (16-G9): The solubility, microsome stability and plasma stability of these two compounds were also determined (Table 2). 18-B3 compound exhibited significantly higher microsome stability as compared to 16-G9 compound. Taken together these data indicates 55152 (18-B3) is a superior scaffold for further derivatization strategy.

TABLE 2

ADME studies

| ID No. | M.W. | LogD LogD(7.4) | Solubility (ug/mL) | | | Microsome Stability % remaining @ 1 hr | | Plasma Stability % remaining @ 3 hrs | |
|---|---|---|---|---|---|---|---|---|---|
| | | | pH 5.0 | pH 6.2 | pH 7.4 | Human | Mouse | Human | Mouse |
| 55153 (18-B3) | 346 | 0.98 | 0.13 | 0.22 | 0.15 | 64.56 | 95.21 | 58.57 | 50.76 |
| 367416 (16-G9) | 282 | 5.09 | 0.16 | 0.22 | 0.2 | 31.64 | 0.57 | 61.25 | 67.74 |

Characterization of 18-B3 derivatives WEIN-159 and WEIN-172: The 18-B3 derivatives were assessed using ELISA assay which revealed multiple derivatives with potential to inhibit WEE1 peigenetic activity. Some of those compounds are shown in Table 3, shown below.

TABLE 3

ELISA assay

| | % Inhibition |
|---|---|
| Phospho-peptide | +Control |
| No peptide | 100 |
| No inhibitor | 0 |
| MK-1775 | 54 |
| SG5-159/WEIN-159 | 118 |
| SG5-124 | 98 |
| G9 | 34 |
| SG5-154 | 105 |
| SG5-172/WEIN-172 | 112 |
| SG5-139/B3 Derivative | 80 |

Figure 7A:
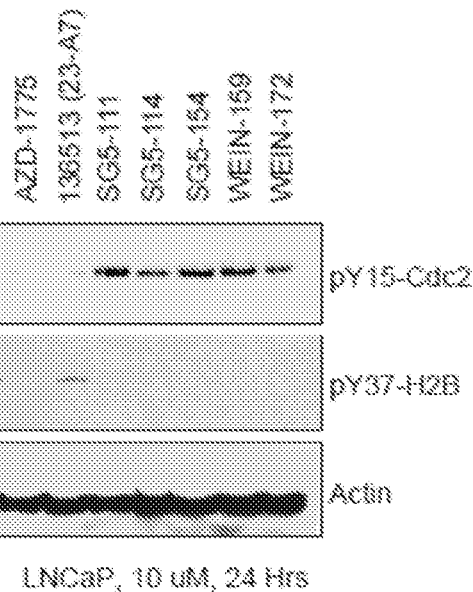
FIGS. 7A-7C show identification of WEIN-159 as a potent WEE1 epigenetic inhibitor.

Five of these compounds, SG5-111, SG5-114, SG5-154, SG5-159 (renamed as WEIN-159) and SG5-172 (WEIN-172) were selected for further characterization in vivo. LNCaP cells were treated with these 5 compounds and H2B & Cdc Tyr-phopshorylation was examined. All these 5 compounds exhibited almost complete loss of H2B Tyr37-phopshorylation, however, Cdc Tyr-phopshorylation was unaffected, indicating high WEE1 epigenetic inhibitory activity (FIG. 7A).

Figure 7B:
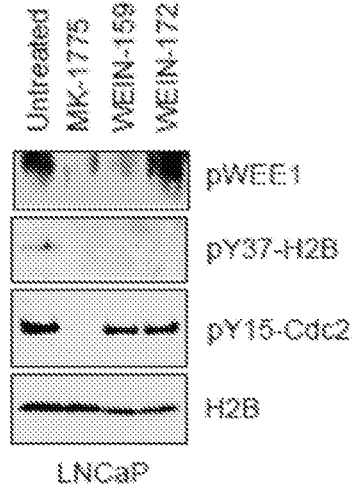
Figure 8A:
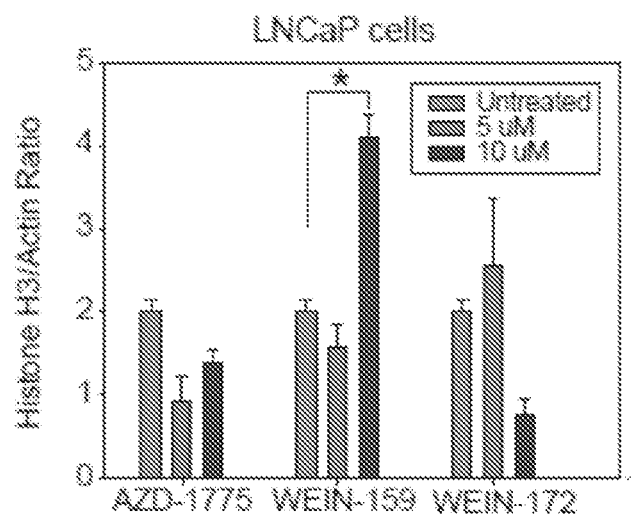
FIGS. 8A-8B show inhibition of WEE1 epigenetic activity lead to increased global histone expression.
Figure 8B:
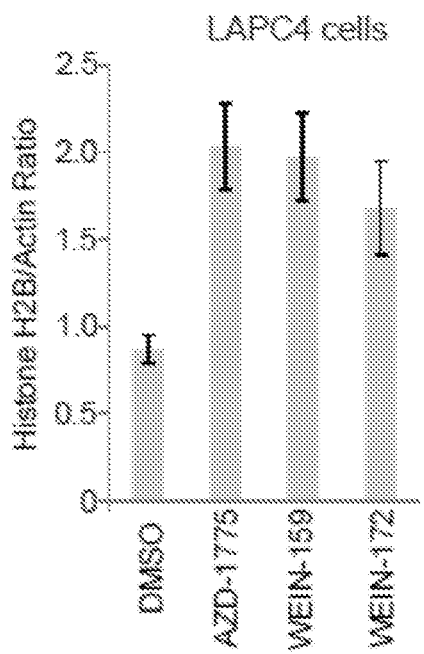
Figures 9A, 9B:
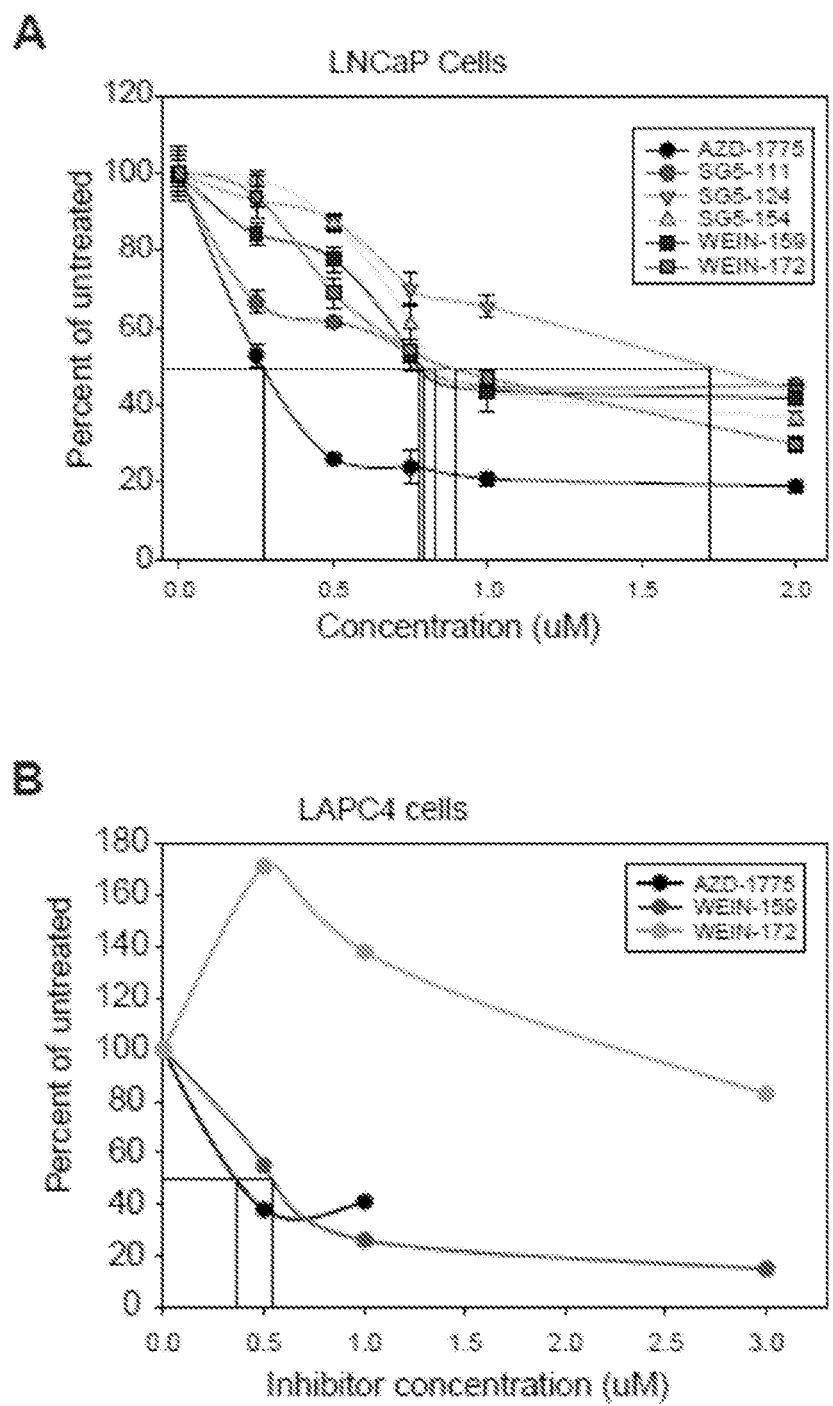
FIGS. 9A-9B show inhibition of WEE1 epigenetic activity compromises cell proliferation.

WEIN-159 and WEIN-172 were further assessed by treatment of LNCaP and melanoma cell line B16, followed by determination of WEE1, H2B and Cdc Tyr-phopshorylation. A significant loss of WEE1 and H2B Tyr-phopshorylation was observed upon WEIN-159 and WEIN-172 treatment, however, Cdc Tyr15-phopshorylation remained unaffected (FIGS. 7B and C). In addition, significant increase in global histone levels was observed as measured by real time PCR of H3 and H2B (FIGS. 8A and B). A cell proliferation assay of LNCaP and LAPC4 cells was performed which revealed $IC_{50}$ of 0.75 µM in LNCaP cells and 0.55 µM in LAPC4 cells for WEIN-159 compound (FIG. 9).

Binding study of WEE1 epigenetic inhibitors: To identify the precise binding region/domain of WEE1 epigenetic inhibitors, WEE1 & WEE2 (as control) kinase domains from mammalian cells (HEK293T cells) were purified. The binding of inhibitors was assessed using Differential Scanning Fluorimetry (DSF). None of the compounds were able to bind to WEE1 or WEE2 kinase domain, in contrast, AZD-1775 that is known to bind ATP-binding pocket of kinase domain was able to bind (Table 4).

TABLE 4

Differential Scanning Fluorimetry (DSF)

| Compound | ΔTm for Wee1 KD (° C.) | ΔTm for Wee2 KD (° C.) |
|---|---|---|
| DMSO | 0.0 | 0.0 |
| SG5-061 (in-house 18-B3) | 0.5 | 0.1 |
| 16-G9 | 0.4 | 0.1 |
| 367416 (16-G9) | 0.5 | −0.1 |
| 35843 (18-B3 derivative) | 0.1 | −0.2 |
| 53313 (18-B3 derivative) | 0.3 | 0.0 |
| 55152 (18-B3) | 0.8 | 1.1 |
| 55153 (18-B3 derivative) | 0.5 | −0.1 |
| 55155 (18-B3 derivative) | 0.1 | 0.0 |
| 59691 (A8 derivative) | −0.3 | −0.3 |

TABLE 4-continued

Differential Scanning Fluorimetry (DSF)

| Compound | ΔTm for Wee1 KD (° C.) | ΔTm for Wee2 KD (° C.) |
|---|---|---|
| 147740 (H9 derivative) | 0.1 | −0.1 |
| AZD-1775 | 16.2 | 11.9 |

Figure 10:
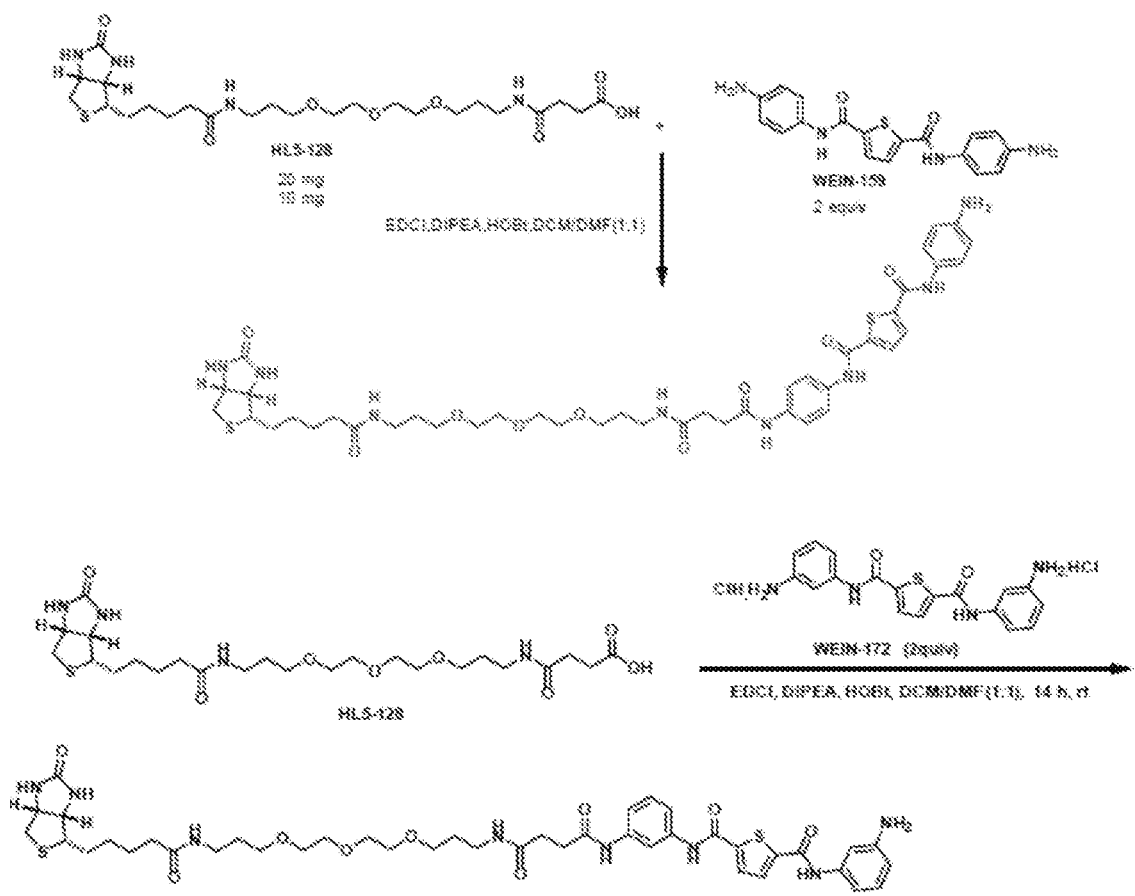
FIG. 10 shows synthesis of biotin conjugates.

Inhibitory activity of WEIN-159 and WEIN-172 was further validated by examining its direct-binding to WEE1 protein, using a pull-down assay. WEIN-159 and WEIN-172 were attached to biotin molecule (FIG. 10) and then immobilized onto streptavidin beads. Beads were incubated with cell lysate, washed and electrophoresed followed by immunoblottng with WEE1 antibodies. WEE1 protein was observed to be bound to WEIN-159 and to lesser extent WEIN-172, however, very little binding was noticed when beads alone were incubated with lysate, indicating direct binding of WEIN-159 to WEE1 protein (FIG. 11A).

Figures 11A, 11B, 11C, 11D, 11E:
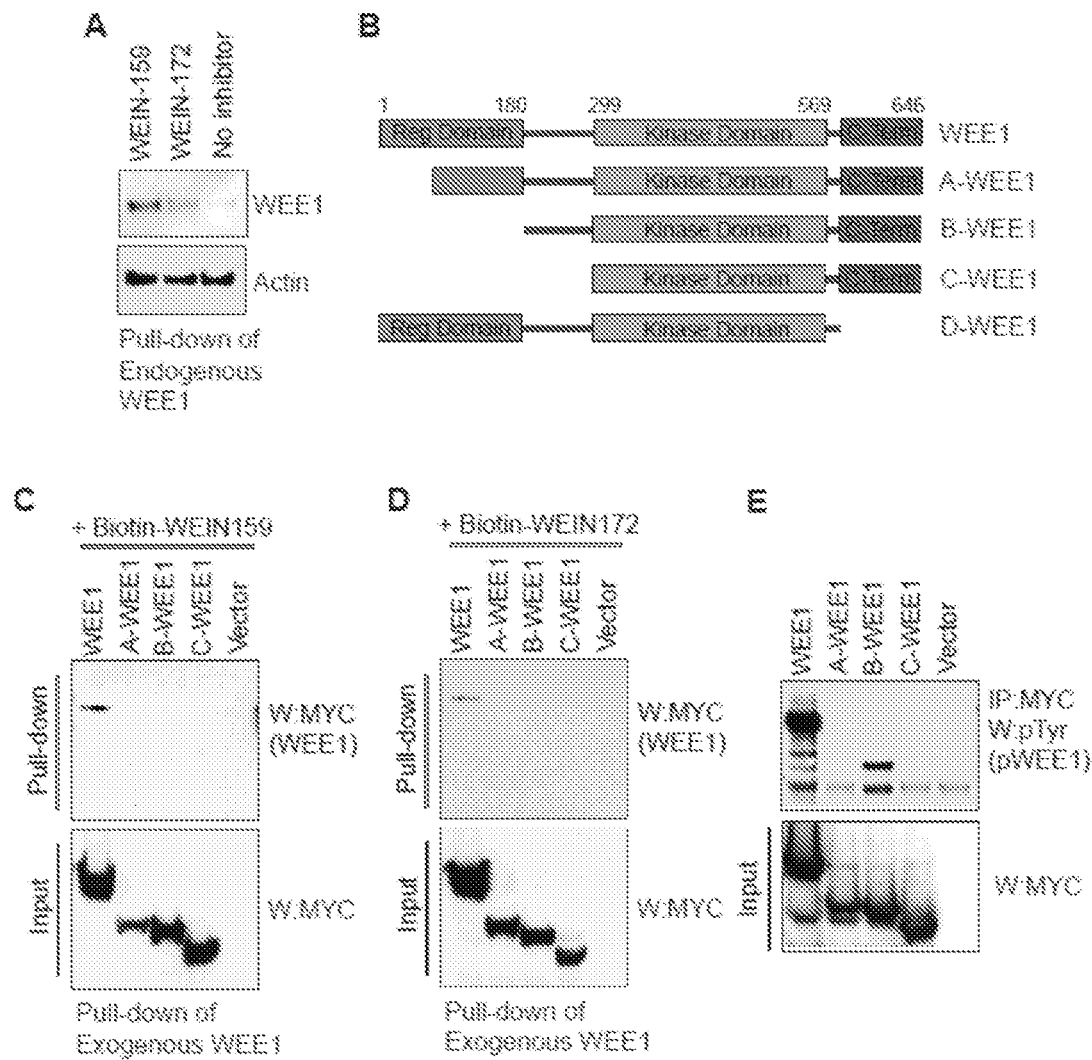
FIGS. 11A-11E show direct interaction between inhibitor and WEE1 kinase.

To further identify region within WEE1 that may be involved in binding to inhibitor, a deletion strategy was employed wherein three deletions, A-WEE1, B-WEE1 and C-Wee1 were generated which were Myc-tagged (FIG. 11B). Constructs were transfected in HEK293T cells and lysates were incubated with biotin beads with bound WEIN-159 and 172. The pull-down experiment revealed that only full length WEE1 interacted with inhibitor and any deletion to WEE1 amino-terminus significantly compromised its binding (FIGS. 11C and D). These data indicates that WEIN-159 and 172 are likely to make contact with amino-terminal regulatory domain of WEE1 kinase. Taken together these data suggests that these are 'allosteric' inhibitors, i.e. those which do not bind to ATP-binding pocket of kinase.

Figure 7C:
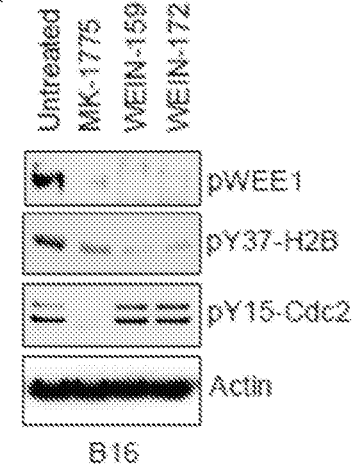

WEIN-159/172 failed to suppress WEE1 cell cycle function: WEIN-159 and 172 exhibited almost complete loss of H2B Tyr37-phopshorylation, however, Cdc Tyr-phopshorylation was unaffected (FIG. 7), indicating that these compounds are devoid of cell cycle regulatory function. To further validate this observation, LNCaP cells were treated with WEIN-159 and 172 for 16 hours and cell cycle analysis was performed by propidium iodide staining. LNCaP cells that possess Wt p53, upon treatment with AZD-1775 expectedly failed to employ G1 arrest (less cells in G2/M), and thus more cells were present in G1 and S phase (Table 5). However, when cells were treated with WEIN-159 and 172, LNCaP cells activated WEE1 mediated G2 arrest (more cells in G2/M), suggesting that WEIN-159/172 failed to suppress WEE1 cell cycle regulatory function.

TABLE 5

Cell Cycle Analysis

| Cell type | G1 | S | G2/M |
|---|---|---|---|
| LNCaP Untreated | 50.89 | 32.47 | 16.65 |
| LNCaP — MK-1775 | 56.51 | 39.22 | 4.27 |
| LNCaP — WEIN-159 | 57.11 | 25.43 | 17.45 |
| LNCaP — WEIN-172 | 56.53 | 27.18 | 16.29 |

Figure 12:
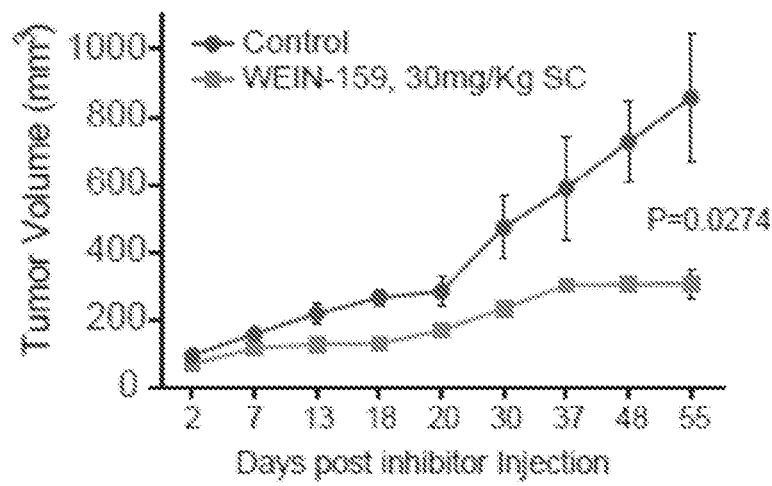
FIG. 12 shows WEIN-159 inhibits prostate xenograft tumor growth. VCaP cells were implanted subcutaneously in male SCID mice. When tumors became palpable, mice were injected either with vehicle 10% DMSO and 90% Cyclodextrin (of 5% stock) or WEIN-159 (30 mg/Kg, re-suspended in 10% DMSO and 90% Cyclodextrin (of 5% stock), for 5 days a week for 4 weeks (n=7 mice for each treatment). Tumor volumes were measured with calipers.

Targeting the WEE1 Epigenetic Activity Mitigates Prostate Tumor Growth: To investigate the effect of WEIN-159 on xenograft tumor growth, VCaP cells were implanted subcutaneously in male SCID mice. When the tumors reached approximately 100 mm³ in size, the mice were randomized and injected five times a week with either the vehicle, 10% DMSO and 90% Cyclodextrin (of 5% stock) or WEIN-159 (30 mg/Kg, re-suspended in 10% DMSO and 90% Cyclodextrin (5% stock). Although vehicle-treated mice formed robust subcutaneous xenograft tumors, tumor growth was significantly compromised in the WEIN-159-injected mice (FIG. 12).

Figure 13:
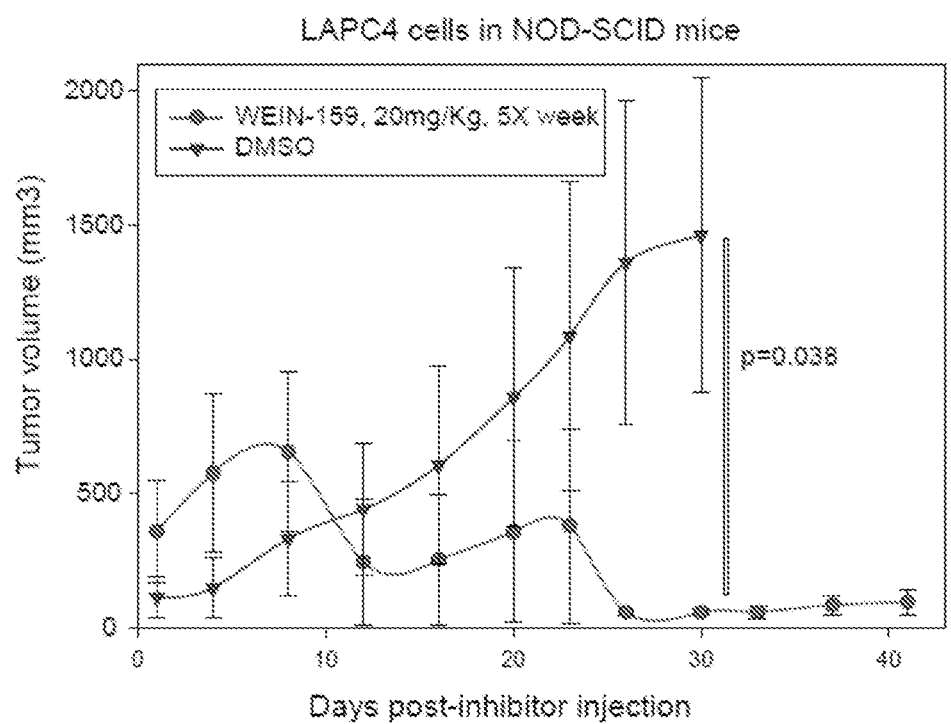
FIG. 13 shows WEIN-159 suppresses prostate xenograft tumor growth. LAPC4 cells were implanted subcutaneously in male NOD-SCID mice. When tumors became palpable, mice were injected either with vehicle (10% DMSO in Phosphate buffered saline) or WEIN-159 (30 mg/kg of body weight) for 5 days a week for 4 weeks (n=7 mice for each treatment). Tumor volumes were measured with calipers.

The effect of WEIN-159 in another prostate xenograft model, LAPC4 was also assessed. The cells were implanted subcutaneously in male NOD-SCID mice and when the tumors reached approximately 100 mm$^3$ in size, the mice were randomized and injected five times a week with either the vehicle (10% DMSO) or WEIN-159 (20 mg/Kg). Similar to VCaP, LAPC4 xenograft tumors too responded to WEIN-159 treatment with a significant reduction in xenograft tumor growth (FIG. 13).

Figure 14:
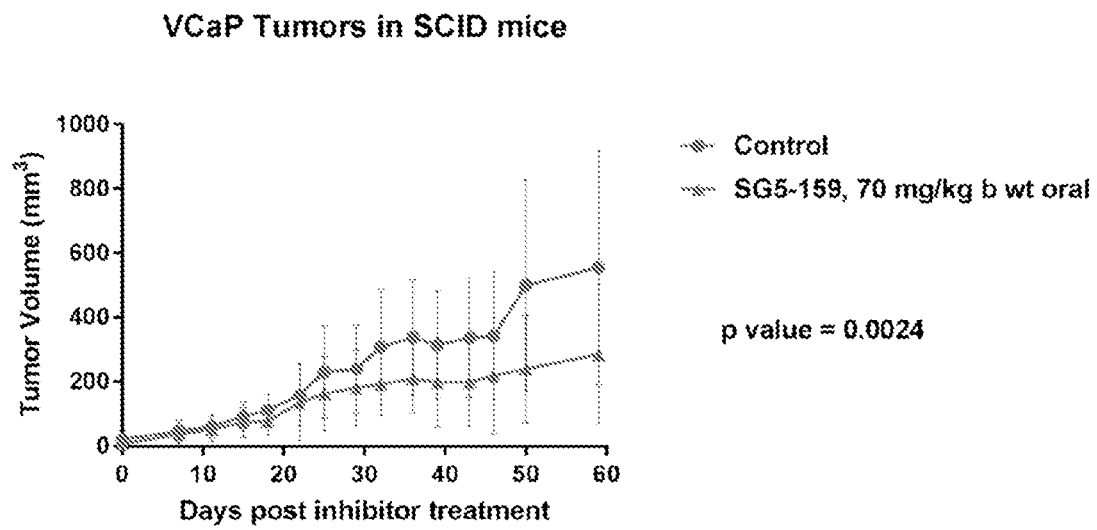
FIG. 14 shows WEIN-159 inhibits prostate tumor growth. VCaP cells were implanted subcutaneously in male NOD-SCID mice. When tumors became palpable, mice were given oral gavage either with vehicle (10% DMSO and 90% PEG300) or WEIN-159 (10% DMSO and 90% PEG300) at 70 mg/kg of body weight for 5 days a week for 4 weeks (n=11 mice for each treatment). Tumor volumes were measured with calipers.

Further, the effect of WEIN-159 in terms of its ability to act as an oral therapeutic compound was assessed. VCaP cells were implanted subcutaneously in male SCID mice. When the tumors reached approximately 100 mm$^3$ in size, the mice were randomized and given oral gavage five times a week with either the vehicle (10% DMSO and 90% PEG 300) or WEIN-159 (30 mg/Kg, re-suspended in 10% DMSO and 90% PEG 300. Although vehicle-treated mice formed robust subcutaneous xenograft tumors, tumor growth was significantly compromised in the WEIN-159-treated mice (FIG. 14).

Figures 15A, 15B:
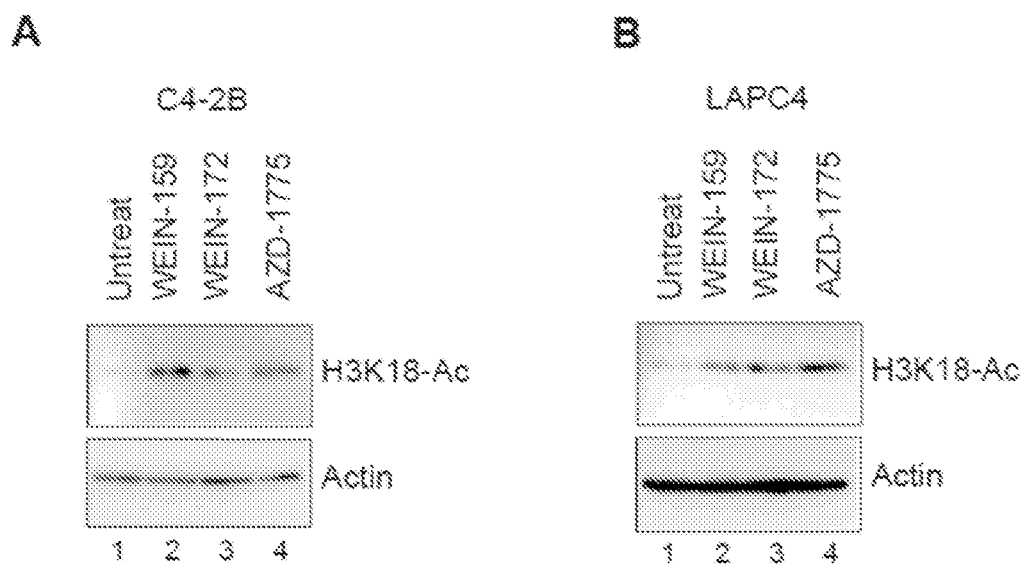
FIGS. 15A-15B show restoration of H3K18 epigenetic marks by epigenetic inhibitor of WEE1 kinase.
Figures 16A, 16B, 16C, 16D:
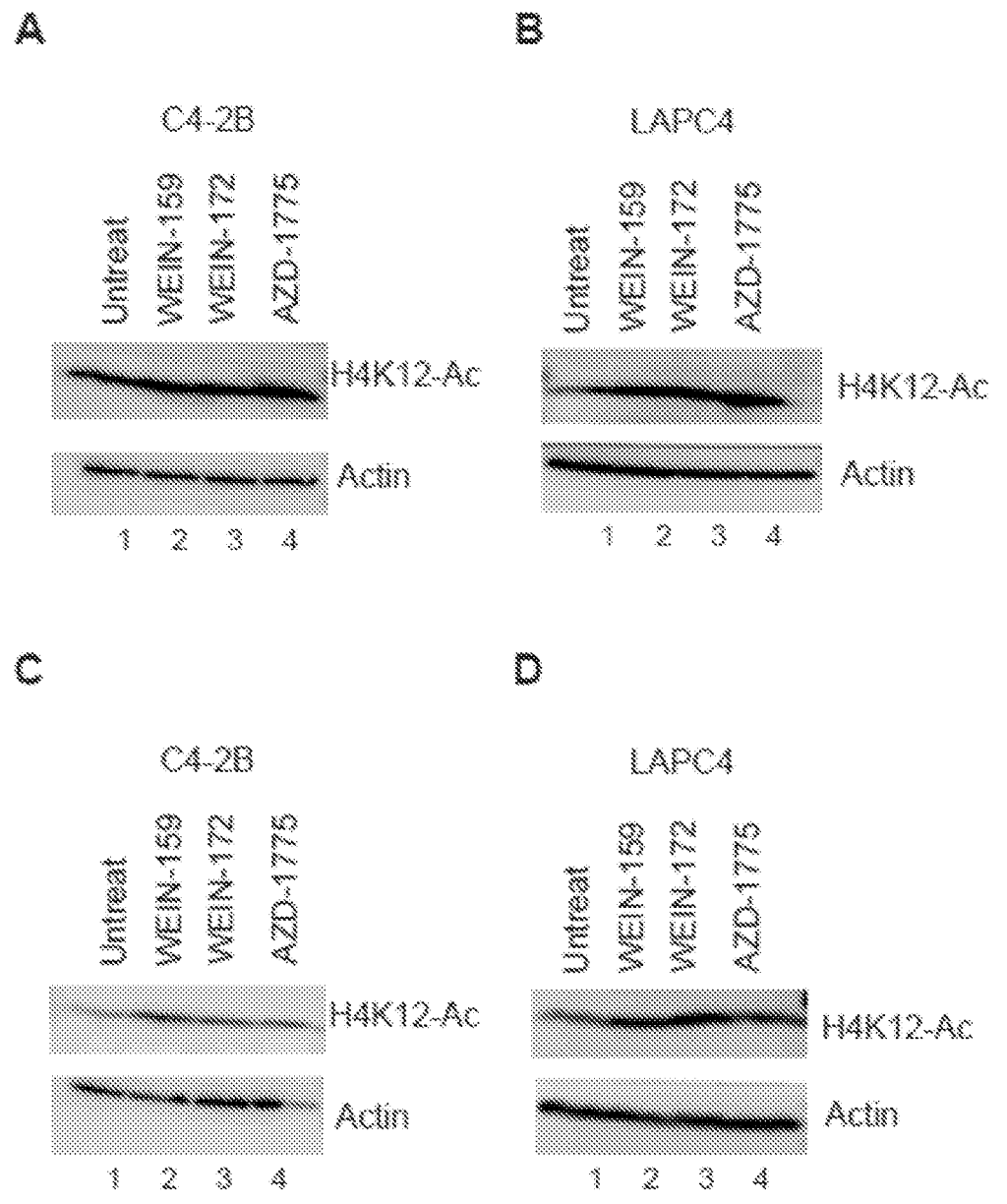
Figure 17A:
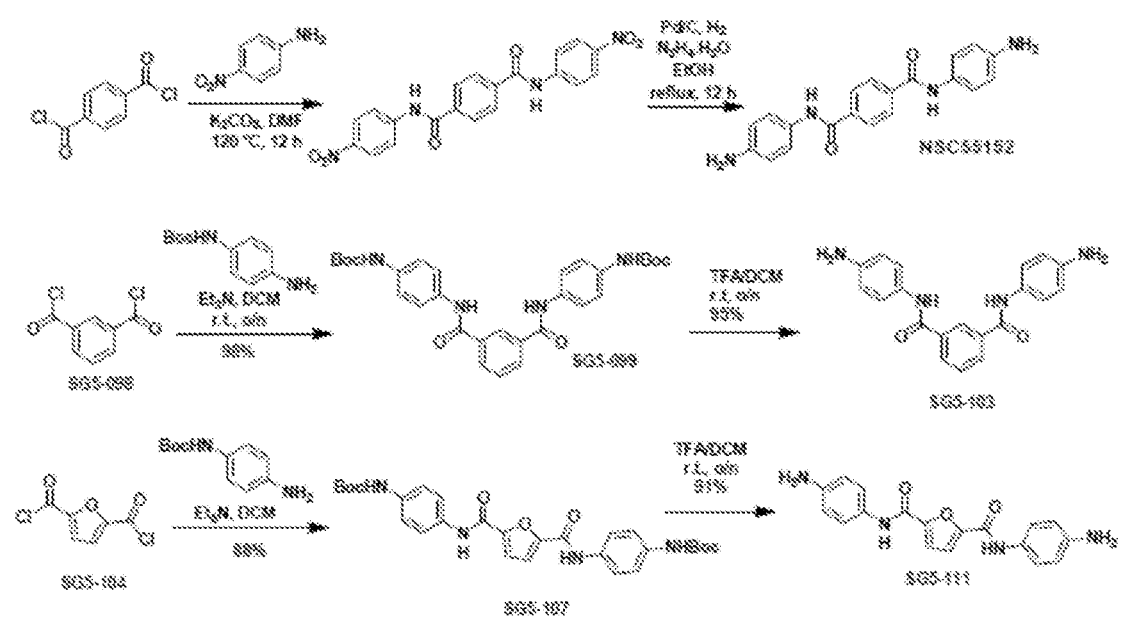
FIG. 17A shows examples of bis-amides related to NSC55152. A series of bis-amides related to NSC55152 were prepared from bis-acyl chlorides and nitro-substituted anilines. The nitro group was reduced to its corresponding aniline by catalytic hydrogenation. Alternatively, an aniline bearing a protected amine group (usually as a tert-butylcarbonyl derivative) was reacted with a bis-acyl chloride to give a protected bis amide (e.g. SG5-099). Treatment of the bis-Boc derivative with strong acid resulted in deprotection of the masked aniline group to provide the bis-aniline SG5-103. Heterocyclic bis-acyl chlorides, such as SG5-104 gave the furan-bis-amide SG5-111. The general route to NSC55152 analogs is shown in FIG. 2, whereby Wee1 inhibitors are prepared by reaction of substituted a substituted phenyl or heterocyclic bis-acyl chloride 1 with N-protected anilines 2 to provide the bis-amide 3. Treatment of 3 with acid effected the deprotection reaction to provide the bis-anilino-bis-amide derivatives 4. Examples are provided in Table 1.
Figure 17B:
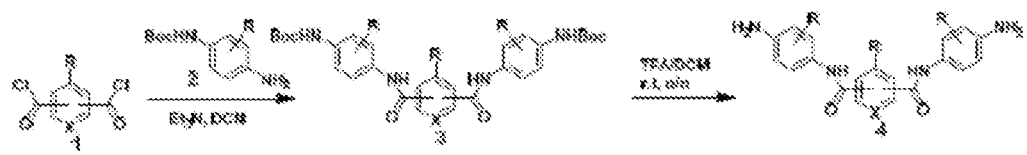
FIG. 17B shows the general route to bis-amides related to NSC55152.

Global upregulation of histone H3K18 and H3K12 acetylation upon WEIN-159 treatment: To further examine the effect of WEE1 inhibition, global histone H3K18, H3K12 and H3K9 and H4K5 acetylation was examined following WEIN-159 and WEIN-172 treatment. A significant increase in H3K18 acetylation (FIG. 15), H3K12 acetylation (FIGS. 16 A and B), and H4K5 acetylation (FIGS. 16A and C), was observed following WEIN-159 and WEIN-172 treatment. In contrast, H3K9 acetylation levels were not affected.

H3K18 acetylation shows a robust peak at the transcription start site (TSS) of active and poised genes, whereas H4K5ac, are elevated in the promoter and transcribed regions of active genes. It was demonstrated previously that lower global/cellular levels of histone H3 lysine 18 acetylation (H3K18ac) predict a higher risk of prostate cancer recurrence. Further, the cellular levels of H3K18ac also predict clinical outcome in both lung and kidney cancer patients, with lower levels predicting significantly poorer survival probabilities.

WEE1 recruits SIRT7 and HDAC3 to suppress global histone H3K18 and H3K12 acetylation: Revitalization of Tumor Suppressor Landscape by WEE1 Inhibitor: Interestingly, *Listeria monocytogenes* induces deacetylation of H3K18. This modification is mediated by the host deacetylase SIRT2. Upon infection, SIRT2 translocates from the cytosol to the chromatin of the host at the transcription start sites of a subset of genes that are repressed. Further, infecting cells in which SIRT2 activity was blocked, resulted in a significant impairment of bacterial infection, showing that activity of SIRT2 is necessary for infection.

Discussion: The discovery of H2B Y37-phosphorylation by WEE1 provides a direct link between the cell cycle kinase and an epigenetic mark that helps to maintain chromatin homeostasis. This finding raises an important question of whether WEE1 utilizes its ability to phosphorylate H2B to accomplish its other well-known function as a mitotic gatekeeper. This expands the perspective of how the role of WEE1 in cell cycle regulation and its role in various malignancies are defined, especially those which over express WEE1 kinase; these cancer cells could utilize alterations in histone levels to confer selective proliferative advantage and radioresistance.

One significant question is how the WEE1-mediated cytoplasmic signaling cascade (WEE1/CDK1) converges with WEE1-mediated nuclear events (WEE1/H2B) to coordinately regulate cell cycle progression. WEE1 phosphorylates H2B at the end of S phase when the peak phosphorylation of its other substrate, CDK1, is receding. This opens up the possibility that when WEE1 senses completion of DNA synthesis, it switches its substrate preference from CDK1 to H2B. In eukaryotes the origin recognition complex (ORC), Cdc6 protein, and the minichromosome maintenance (MCM) protein complex assemble on chromatin before initiation of DNA replication. CDK1 has been shown to interact specifically with the ORCs in mammalian, *Xenopus*, and yeast cells. CDKs regulate DNA replication positively by inducing the initiation of DNA replication at the $G_1/S$ transition and negatively by preventing further rounds of origin firing. WEE1 phosphorylates CDK1 in S phase thus preventing further rounds of origin firing within the same cell cycle. Thus, it is likely that upon completion of DNA synthesis, when WEE1 is prevented from phosphorylating CDK1, it switches to a new substrate, H2B. Thus, by integrating these two seemingly distinct temporal events, WEE1 promotes progression into mitosis with accurately duplicated chromatin.

Identification of WEE1 epigenetic activity raises several important questions in normal physiology as well as in disease pathology. Are there auxiliary loci epigenetically marked by pY37-H2B modification in cancers with aberrant WEE1 expression? If so, do cancer cells employ a different set of epigenetic readers to read H2B Y37-phosphorylation and are there common motifs that distinguish the promoters marked with this specific modification? It is still unclear at this point if pY37-H2B modulates chromatin architecture by recruiting chromatin-remodeling proteins and thereby impacting patterns of local gene expression. Another area to explore is whether this histone Tyr-modification potentially cross talks with other histone modifications such as the H4K5 and H3K12 and H3K18 acetylation, which have known roles in chromatin replication or repair.

Cancer is a complex disease, differences in biology and outcomes exist not only among various clinical states but also within each patient. Personalized medicine offers the potential to optimize treatment for a given patient, based on molecular biomarkers that drive individual variability or drug responses. Thus, elucidation of abundant WEE1 expression and H2B Y37-phosphorylation in a subset of GBM, TNBC or malignant melanoma tumor biopsies could be a strong rationale for administration of WEE1 epigenetic inhibitor. This 'personalized therapy' for a subset of WEE1-positive GBM, TNBC or malignant melanoma patients could be a significant development as limited therapeutic options and no targeted therapeutic modalities are currently available for these cancers with low survival rates.

Chemistry Methods.

Method A: Acyl chloride (0.5 equiv.) was added into a mixture of amine (1 equiv.) and triethylamine (1 equiv.) in DCM (~0.2 M). The mixture was stirred at room temperature. EtOAc (50 mL) was added and washed with water (2×50 mL) and brine (1×50 mL), and concentrated under reduced pressure. The resulting residue was triturated using EtOH/hexanes and the solids were washed with hexanes and water, and dried.

Method B: Boc-protected material was stirred in TFA/DCM (1:1) at room temperature. The mixture was concentrated under reduced pressure and the resulting residue was stirred in saturated sodium bicarbonate. The precipitates were filtered and washed with water. The resulting solid was triturated using EtOH/hexanes to provide the desired product.

Method C: Boc-protected material was stirred in 4 M HCl in MeOH and/or 4 M HCl in dioxane. Upon completion, the mixture was concentrated under reduced pressure. The resulting residue was triturated using MeOH/EtOAc to provide the desired product as HCl salts.

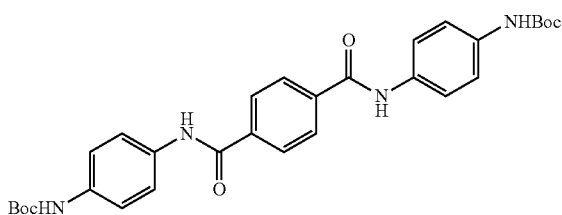 [SMILES: CC(C)(C)OC(=O)Nc1ccc(NC(=O)c2ccc(C(=O)Nc3ccc(NC(=O)OC(C)(C)C)cc3)cc2)cc1]

Di-tert-utyl ((terephthaloylbis(azanediyl))bis(4,1-phenylene))dicarbamate (SG5-060): This was prepared from tert-butyl (4-aminophenyl)carbamate (416 mg, 2 mmol), terephthaloyl dichloride (203 mg, 1 mmol), triethylamine (0.280 mL, 2 mmol), and DCM (10 mL) using Method A (reaction time, 15 h) to give the title compound as a light pink solid (540 mg, 99%). $^1$H NMR (400 MHz, DMSO-$d_6$) δ 10.29 (s, 2H), 9.31 (s, 2H, reduced by 50% on $D_2O$ shake), 8.05 (s, 4H), 7.64 (d, J=8.9 Hz, 4H), 7.41 (d, J=8.9 Hz, 4H), 1.46 (s, 18H).

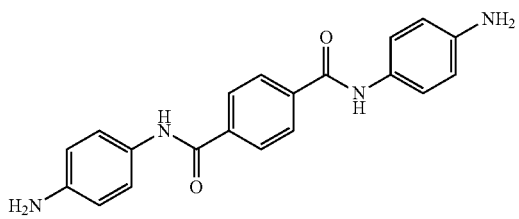 [SMILES: Nc1ccc(NC(=O)c2ccc(C(=O)Nc3ccc(N)cc3)cc2)cc1]

$N^1,N^4$-bis(4-aminophenyl)terephthalamide (SG5-061): This was prepared from SG5-060 (500 mg, 0.914 mmol) and TFA/DCM (1:1, 5 mL) using Method B (reaction time, 1 h) to give the title compound as an off-white solid (243.12 mg, 77%). HPLC: 99% [$t_R$=5.1 min, 20% MeOH, 80% water (with 0.1% TFA), 20 min]. $^1$H NMR (400 MHz, DMSO-$d_6$) δ 9.97 (s, 2H), 8.00 (s, 4H), 7.37 (d, J=8.7 Hz, 4H), 6.53 (d, J=8.7 Hz, 4H), 4.94 (s, 4H, disappeared on D20 shake). HPLC-MS (ESI+): m/z 347.1 [30%, (M+H)$^+$]. LC-MS (ESI+): 369.1 [35%, (M+H)$^+$], 347.1 [100%, (M+H)$^+$]. HRMS (ESI+): m/z calcd for $C_{20}H_{18}N_4O_2$ (M+H)$^+$ 347.1502, found 347.1486.

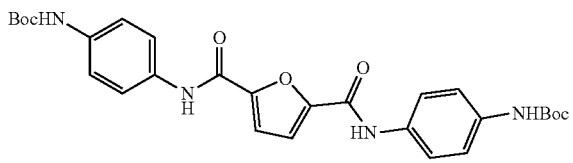 [SMILES: CC(C)(C)OC(=O)Nc1ccc(NC(=O)c2ccc(C(=O)Nc3ccc(NC(=O)OC(C)(C)C)cc3)o2)cc1]

Di-tert-butyl (((furan-2,5-dicarbonyl)bis(azanediyl))bis (4,1-phenylene))dicarbamate (SG5-107): This was prepared from tert-butyl (4-aminophenyl)carbamate (208 mg, 1 mmol), furan-2,5-dicarbonyl dichloride (96 mg, 0.5 mmol), triethylamine (0.140 mL, 1 mmol), and DCM (5 mL) using Method A (reaction time, 15 h) to give the title compound as an off-white solid (236.99 mg, 88%). $^1$H NMR (400 MHz, DMSO-$d_6$) δ 10.17 (s, 2H, reduced by 50% on $D_2O$ shake), 9.37 (s, 2H, disappeared on $D_2O$ shake), 7.58 (d, J=8.9 Hz, 4H), 7.45 (d, J=8.9 Hz, 4H), 7.35 (s, 2H), 1.46 (s, 19H). HPLC-MS (ESI+): m/z 559.3 [50%, (M+Na)$^+$].

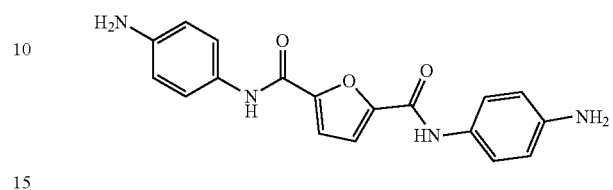

$N^2,N^5$-bis(4-aminophenyl)furan-2,5-dicarboxamide (SG5-111): This was prepared from SG5-107 (230 mg, 0.428 mmol) and TFA/DCM (1:1, 5 mL) using Method B (reaction time, 1 h) to give the title compound as a yellow solid (131.76 mg, 91%). HPLC: >99% [$t_R$=4.5 min, 30% MeOH, 70% water (with 0.1% TFA), 20 min]. $^1$H NMR (400 MHz, DMSO-$d_6$) δ 9.90 (s, 2H, disappeared on $D_2O$ shake), 7.30 (d, J=8.5 Hz, 4H), 7.25 (s, 2H), 6.56 (d, J=8.5 Hz, 4H), 5.04 (s, 4H, disappeared on $D_2O$ shake). HPLC-MS (ESI+): m/z 337.2 [50%, (M+H)$^+$], 169.2 [100%, (M+2H)$^{2+}$]. LC-MS (ESI+): 695.2 [50%, (2M+Na)$^{2+}$], 359.1 [100%, (M+Na)$^+$], 337.2 [25%, (M+H)$^+$]. HRMS (ESI+): m/z calcd for $C_{18}H_{16}N_4O_3$ (M+Na)$^+$ 359.1115, found 359.1119.

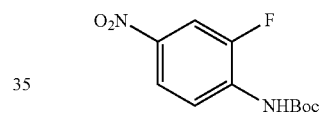

tert-Butyl (2-fluoro-4-nitrophenyl)carbamate (SG5-101): A mixture of 2-fluoro-4-nitroaniline (3.9 g, 25 mmol), $Boc_2O$ (5.73 g, 26.25 mmol), trimethylamine (5.23 mL, 37.5 mmol), and DMAP (305.43 mg, 2.5 mmol) in DCM (35 mL) was stirred at room temperature for 24 h. DCM was removed and the resulting residue was added EtOAc (25 mL) and hexanes (50 mL). Upon filtration, the precipitates were removed and the filtrate was concentrated under reduced pressure. The resulting oil was dissolved in EtOAc (100 mL), washed with water (100 mL), dried ($Na_2SO_4$), and concentrated under reduced pressure. MeOH (35 mL) and THF (15 mL) were added, followed by NaOH (1 g, 30 mmol), and stirred at room temperature for 1 h. EtOAc was added, washed with 1 M HCl (aq), water, and brine (50 mL each), dried ($Na_2SO_4$), and concentrated under reduced pressure. The resulting residue was purified by chromatography ($SiO_2$) eluting with hexanes (with 0-10% EtOAc) to provide the title compound as a light yellow solid (4.315 g, 67%). $^1$H NMR (400 MHz, $CDCl_3$) δ 8.41-8.33 (m, 1H), 8.06 (ddd, J=9.2, 2.5, 1.3 Hz, 1H), 7.97 (dd, J=10.9, 2.5 Hz, 1H), 7.00 (s, 1H), 1.54 (s, 9H). $^{19}$F NMR (376 MHz, DMSO-$d_6$) δ -129.81 (s).

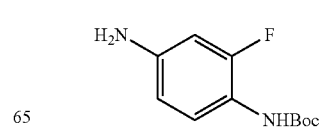

tert-Butyl (4-amino-2-fluorophenyl)carbamate (SG5-112): Into a mixture of SG5-101 (4.20 g, 16.38 mmol) in MeOH (50 mL, deoxygenated with Argon gas) was added Pd/C (10% w/w, 750 mg) under Argon. The flask was evacuated and back filled with Argon (twice). Argon gas was evacuated and a balloon of hydrogen was attached to the system. The reaction mixture was stirred at room temperature overnight. Then, the mixture was filtered using a short plug of Celite, washed with MeOH (150 mL), and concentrated under reduced pressure to provide the title compound as a brown oil (3.28 g, 89%). $^1$H NMR (400 MHz, Chloroform-d) δ 7.68 (br s, 1H), 6.50-6.23 (m, 3H; 1H disappeared on D$_2$O shake), 3.58 (s, 2H, disappeared on D$_2$O shake), 1.50 (s, 9H). $^{19}$F NMR (376 MHz, DMSO-d$_6$) δ −130.24 (s).

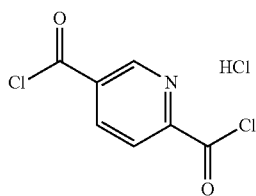 [SMILES: O=C(Cl)c1ccc(C(=O)Cl)nc1 ; Cl]

(2,5-Bis(chlorocarbonyl)pyridin-1-ium-1-yl)hydridochlorate(I) (SG5-115): A mixture of pyridine-2,5-dicarboxylic acid (5 g, 29.92 mmol) in thionyl chloride (10 mL) was heated at reflux overnight. The mixture was concentrated under reduced pressure to provide the title compound as an HCl salt (5.593 g, 78%). $^1$H NMR (400 MHz, DMSO-d$_6$) δ 13.87 (s, 1H), 9.12 (dd, J=2.1, 0.8 Hz, 1H), 8.41 (dd, J=8.1, 2.1 Hz, 1H), 8.12 (dd, J=8.1, 0.8 Hz, 1H). $^{13}$C NMR (101 MHz, DMSO-d$_6$) δ 165.8, 165.8, 151.5, 150.3, 139.0, 129.4, 125.0.

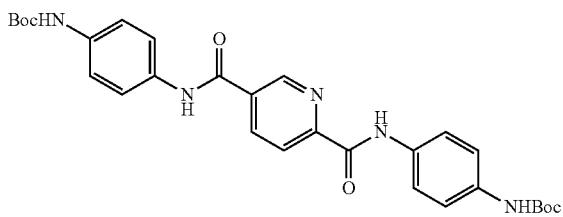 [SMILES: CC(C)(C)OC(=O)Nc1ccc(NC(=O)c2ccc(C(=O)Nc3ccc(NC(=O)OC(C)(C)C)cc3)nc2)cc1]

Di-tert-butyl (((pyridine-2,5-dicarbonyl)bis(azanediyl))bis(4,1-phenylene))dicarbamate (SG5-119): This was prepared from tert-butyl (4-aminophenyl)carbamate (108 mg, 0.5 mmol), SG5-115 (60 mg, 0.25 mmol), triethylamine (0.070 mL, 0.5 mmol), and DCM (2.5 mL) using Method A (reaction time, 15 h) to give the title compound as an off-white solid (97.24 mg, 70%). $^1$H NMR (400 MHz, DMSO-d$_6$) δ 10.65 (s, 1H), 10.52 (s, 1H), 9.34 (d, J=9.5 Hz, 2H), 9.15 (dd, J=2.1, 0.7 Hz, 1H), 8.51 (dd, J=8.2, 2.1 Hz, 1H), 8.24 (dd, J=8.2, 0.7 Hz, 1H), 7.78 (d, J=9.0 Hz, 2H), 7.64 (d, J=9.0 Hz, 2H), 7.48-7.38 (m, 4H), 1.46 (s, 18H). HPLC-MS (ESI+): m/z 548.3 [100%, (M+H)$^+$].

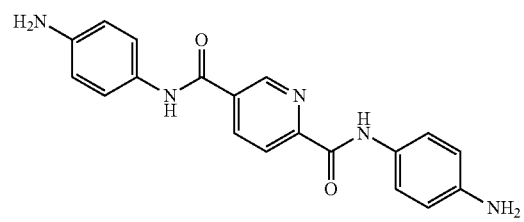 [SMILES: Nc1ccc(NC(=O)c2ccc(C(=O)Nc3ccc(N)cc3)nc2)cc1]

N$^2$,N$^5$-bis(4-aminophenyl)pyridine-2,5-dicarboxamide (SG5-124): This was prepared from SG5-119 (90 mg, 0.164 mmol) and TFA/DCM (1:1, 5 mL) using Method B (reaction time, 1 h) to give the title compound as a yellow solid (41.10 mg, 72%). HPLC: 99% [t$_R$=9.4 min, 20% MeOH, 80% water (with 0.1% TFA), 20 min]. $^1$H NMR (400 MHz, DMSO-d$_6$) δ 10.34 (s, 1H), 10.22 (s, 1H), 9.11 (dd, J=2.2, 0.7 Hz, 1H), 8.46 (dd, J=8.2, 2.2 Hz, 1H), 8.20 (dd, J=8.2, 0.7 Hz, 1H), 7.53 (d, J=8.8 Hz, 2H), 7.38 (d, J=8.8 Hz, 2H), 6.55 (d, J=8.8 Hz, 2H), 6.54 (d, J=8.8 Hz, 2H), 4.99 (s, 2H), 4.98 (s, 2H). HPLC-MS (ESI+): m/z 348.2 [50%, (M+H)$^+$], 174.7 [100%, (M+2H)$^{2+}$]. LC-MS (ESI+): 717.2 [100%, (2M+Na)$^{2+}$], 370.1 [65%, (M+Na)$^+$], 348.1 [50%, (M+H)$^+$]. HRMS (ESI+): m/z calcd for C$_{19}$H$_{17}$N$_5$O$_2$ (M+Na)$^+$ 370.1274, found 370.1274.

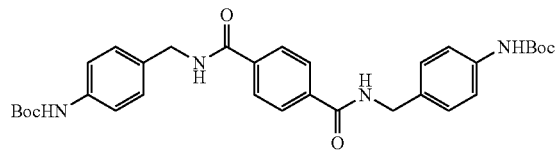 [SMILES: CC(C)(C)OC(=O)Nc1ccc(CNC(=O)c2ccc(C(=O)NCc3ccc(NC(=O)OC(C)(C)C)cc3)cc2)cc1]

Di-tert-butyl (((terephthaloylbis(azanediyl))bis(methylene))bis(4,1-phenylene))dicarbamate (SG5-133-3): This was prepared from tert-butyl (4-(aminomethyl)phenyl)carbamate (111.14 mg, 0.5 mmol), terephthaloyl dichloride (50.75 mg, 0.25 mmol), triethylamine (0.070 mL, 0.5 mmol), and DCM (2.5 mL) using Method A (reaction time, 15 h) to give the title compound as an off-white solid (125.71 mg, 88%). $^1$H NMR (400 MHz, DMSO-d$_6$) δ 9.28 (s, 2H, disappeared on D$_2$O shake), 9.08 (t, J=5.8 Hz, 2H, disappeared on D$_2$O shake), 7.93 (s, 4H), 7.37 (d, J=8.5 Hz, 4H), 7.18 (d, J=8.5 Hz, 4H), 4.38 (d, J=5.8 Hz, 4H), 1.44 (s, 18H). HPLC-MS (ESI+): m/z 597.4 [100%, (M+Na)$^+$].

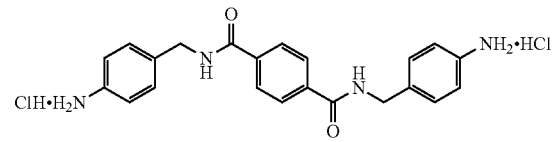

N$^1$,N$^4$-bis(4-aminobenzyl)terephthalamide dihydrochloride (SG5-137-3): This was prepared from SG5-133-3 (115 mg, 0.200 mmol) using Method C (reaction time, overnight at room temperature and overnight at 40° C.) to give the title compound as an off-white solid (85.46 mg, 95%). HPLC: 96% [t$_R$=5.4 min, 20% MeOH, 80% water (with 0.1% TFA), 20 min]. $^1$H NMR (400 MHz, DMSO-d$_6$) δ 10.06 (s, 6H, disappeared on D$_2$O shake), 9.26 (t, J=5.9 Hz, 2H), 7.97 (s, 4H), 7.40 (d, J=8.5 Hz, 4H), 7.28 (d, J=8.5 Hz, 4H), 4.47 (d, J=5.9 Hz, 4H). HPLC-MS (ESI+): m/z 375.2 [70%, (M+H)$^+$]. LC-MS (ESI+): 771.3 [90%, (2M+Na)$^{2+}$], 397.2

[100%, (M+Na)⁺]. HRMS (ESI+): m/z calcd for C₂₂H₂₂N₄O₂ (M+Na)⁺ 397.1635, found 397.1631.

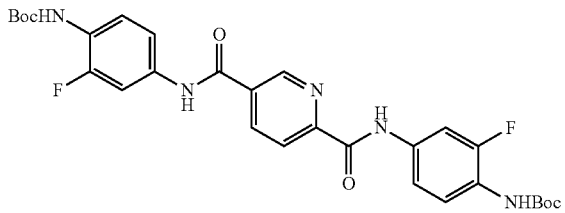 [SMILES: CC(C)(C)OC(=O)Nc1ccc(NC(=O)c2ccc(C(=O)Nc3ccc(NC(=O)OC(C)(C)C)c(F)c3)nc2)cc1F]

Di-tert-butyl ((((pyridine-2,5-dicarbonyl)bis(azanediyl))bis(2-fluoro-4,1-phenylene))dicarbamate (SG5-140-3): This was prepared from SG5-112 (113.13 mg, 0.5 mmol), SG5-115 (60.12 mg, 0.25 mmol), triethylamine (0.070 mL, 0.5 mmol), and DCM (2.5 mL) using Method A (reaction time, overnight) to give the title compound as an off-white solid (72.48 mg, 50%). ¹H NMR (400 MHz, DMSO-d₆) δ 10.93 (s, 1H, disappeared on D₂O shake), 10.74 (s, 1H, disappeared on D₂O shake), 9.17 (dd, J=2.2, 0.7 Hz, 1H), 8.93 (s, 1H, disappeared on D₂O shake), 8.90 (s, 1H, disappeared on D₂O shake), 8.54 (dd, J=8.2, 2.2 Hz, 1H), 8.28 (dd, J=8.2, 0.7 Hz, 1H), 7.88 (dd, J=13.0, 2.3 Hz, 1H), 7.75 (dd, J=13.0, 2.3 Hz, 1H), 7.69 (dd, J=8.9, 1.7 Hz, 1H), 7.60-7.47 (m, 2H), 7.45 (dd, J=8.9, 1.7 Hz, 1H), 1.44 (s, 18H). ¹⁹F NMR (376 MHz, DMSO-d₆) δ −122.38 (s).

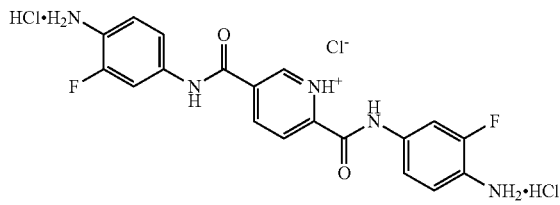

(2,5-Bis((4-amino-3-fluorophenyl)carbamoyl)pyridin-1-ium-1-yl)hydridochlorate(I) dihydrochloride (SG5-147-3): This was prepared from SG5-140-3 (62.79 mg, 0.108 mmol) using Method C (reaction time, overnight at room temperature) to give the title compound as an off-white solid (43.01 mg, 81%). HPLC: 98% [t$_R$=9.0 min, 30% MeOH, 70% water (with 0.1% TFA), 20 min]. ¹H NMR (400 MHz, DMSO-d₆) δ 10.84 (s, 1H), 10.68 (s, 1H), 9.17 (d, J=1.5 Hz, 1H), 8.53 (dd, J=8.2, 2.2 Hz, 1H), 8.26 (d, J=8.6 Hz, 1H), 7.86 (dd, J=13.3, 2.0 Hz, 1H), 7.71 (dd, J=13.2, 1.9 Hz, 1H), 7.62 (d, J=8.8 Hz, 1H), 7.38 (d, J=8.4 Hz, 1H), 7.05 (q, J=9.3 Hz, 2H). ¹⁹F NMR (376 MHz, DMSO-d₆) δ −127.21 (s). HPLC-MS (ESI+): m/z 384.2 [100%, (M+H)⁺], 192.7 [50%, (M+2H)²⁺].

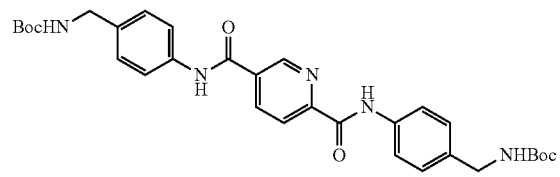 [SMILES: CC(C)(C)OC(=O)NCc1ccc(NC(=O)c2ccc(C(=O)Nc3ccc(CNC(=O)OC(C)(C)C)cc3)nc2)cc1]

Di-tert-butyl (((((pyridine-2,5-dicarbonyl)bis(azanediyl))bis(4,1-phenylene))bis(methylene))dicarbamate (SG5-140-11): This was prepared from tert-butyl (4-aminobenzyl)carbamate (111.15 mg, 0.5 mmol), SG5-115 (60.12 mg, 0.25 mmol), triethylamine (0.070 mL, 0.5 mmol), and DCM (2.5 mL) using Method A (reaction time, overnight) to give the title compound as an off-white solid (78.78 mg, 55%). ¹H NMR (400 MHz, DMSO-d₆) δ 10.74 (s, 1H, disappeared on D₂O shake), 10.60 (s, 1H, disappeared on D₂O shake), 9.17 (dd, J=2.2, 0.6 Hz, 1H), 8.53 (dd, J=8.2, 2.2 Hz, 1H), 8.27 (dd, J=8.2, 0.6 Hz, 1H), 7.84 (d, J=8.4 Hz, 2H), 7.69 (d, J=8.4 Hz, 2H), 7.38 (t, J=5.9 Hz, 2H, disappeared on D₂O shake), 7.84 (d, J=8.4 Hz, 2H), 7.69 (d, J=8.4 Hz, 2H), 4.09 (d, J=5.9 Hz, 4H), 1.38 (s, 18H).

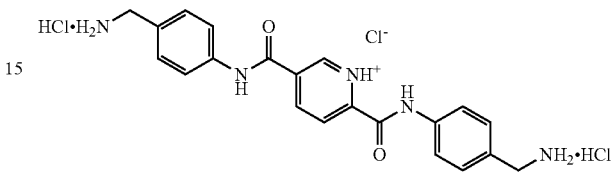

(2,5-Bis((4-(aminomethyl)phenyl)carbamoyl)pyridin-1-ium-1-yl)hydridochlorate(I) dihydrochloride (SG5-147-11): This was prepared from SG5-140-11 (71.89 mg, 0.125 mmol) using Method C (reaction time, overnight at room temperature) to give the title compound as an off-white solid (53.55 mg, 88%). HPLC: 96% [t$_R$=5.2 min, 30% MeOH, 70% water (with 0.1% TFA), 20 min]. ¹H NMR (400 MHz, DMSO-d₆) δ 10.88 (s, 1H, disappeared on D₂O shake), 10.84 (s, 1H, disappeared on D₂O shake), 9.23 (dd, J=2.2, 0.7 Hz, 1H), 8.59 (dd, J=8.2, 2.2 Hz, 1H), 8.41-8.17 (m, 7H; 6H disappeared on D₂O shake), 7.96 (d, J=8.6 Hz, 2H), 7.83 (d, J=8.6 Hz, 2H), 7.48 (d, J=8.6 Hz, 2H), 7.46 (d, J=8.6 Hz, 2H), 4.00 (d, J=5.5 Hz, 4H). HPLC-MS (ESI+): m/z 171.6 [100%, (M+2H-2NH₃)²⁺].

Example: Immunomodulatory Effects of a Small Molecule Inhibitor of WEE1 Kinase, WEIN-159

WEE1 is an important G2 checkpoint kinase that prevents entry into mitosis upon DNA damage. Studies have shown that most cancers have increased WEE1 expression that allows the cancer cells to overcome the mitotic catastrophe and continue proliferation. The role of WEE1 in cell cycle and associated histone synthesis thus, makes it a prime drug target for cancer therapy. Though there are several specific tyrosine kinase inhibitors that majorly work as ATP analogues, drawbacks such as drug resistance and toxicity compromise their efficacy during clinical trials.

As cancer development and progression is majorly influenced by the interaction of cancer cells with the immune cells in the tumor microenvironment, immune modulation also serves to be a prominent method of treatment in cancer patients. Several immune checkpoint inhibitors have been developed to treat a variety of malignancies. However, antagonizing regulatory pathways in certain cancers cause non-responsiveness leading to less successful clinical outcomes.

In an effort to circumvent the gap between conventional chemotherapy and immunotherapy, a small molecule WEE1 inhibitor, WEIN-159, was prepared. WEIN-159 is one of the few non-ATP competitive drug that targets unique allosteric sites for kinase inhibition. The present study aims to explore the immune modulatory potential of WEIN-159 in addition to its ability to inhibit tumor growth by kinase inhibition using syngenic mice model.

Figure 18:
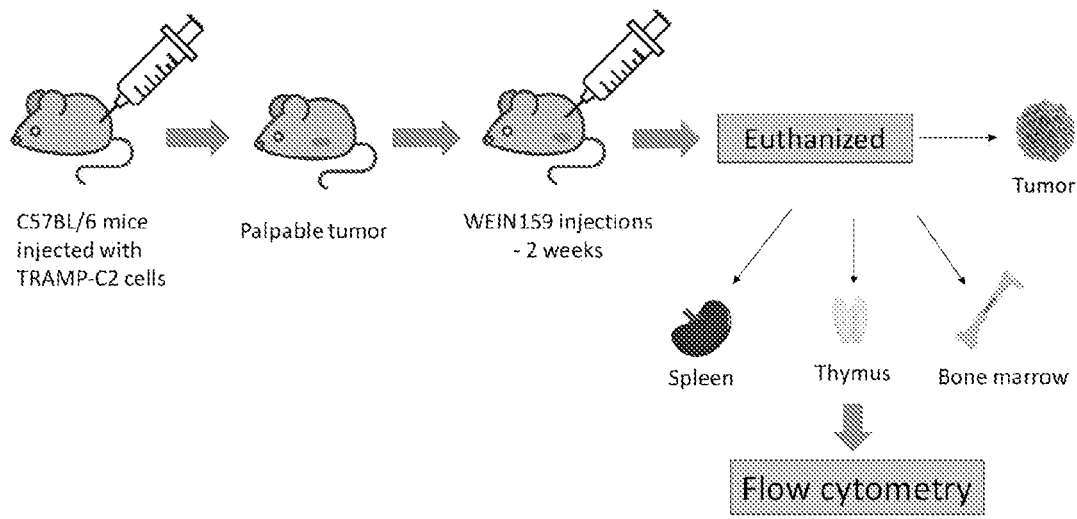
FIG. 18 shows a schematic diagram of an experiment including injecting mice with TRAMP-C2-cell and flow cytometry.

Methods: Mice—C57BL/6 mice were maintained in pathogen-free facilities in accordance with guidelines of the Animal Care and Use Committee at Washington University (St. Louis, Mo.). Cell Line—TRAMP-C2 were grown in DMEM with 4 mM L-glutamine adjusted to contain 1.5 g/L sodium bicarbonate and 4.5 g/L glucose supplemented with 0.005 mg/ml bovine insulin and 10 nM dehydroisoandrosterone, 90% (Sigma, St. Louis, Mo.); 5% FBS and 5% Nu-Serum IV, at 37° C. in 5% $CO_2$ incubator. Syngenic Mice Model—$2\times10^6$ TRAMP-C2 cells were suspended in PBS and mixed with matrigel (BD Biosciences) in the ratio 1:1 and were implanted subcutaneously into the dorsal flank of five-six weeks old C57BL/6 mice. Once the tumors became palpable, mice were injected subcutaneously with either vehicle (5% cyclodextrin+10% DMSO) or WEIN-159 (30 mg/kg of body weight), five times a week, for 4 weeks. Tumor volumes were measured twice weekly using calipers. At the end of the study, all mice were humanely euthanized, tumors extracted and weighed. Spleen, thymus and bone marrow were collected and immunophenotyping was done using flow cytometry (See FIG. 18).

Preparation of immune cells and flow cytometry—Single cell suspensions were made from spleen, thymus and bone marrow. $2\times10^6$ cells were counted using trypan blue assay and stained with Aqua Live/Dead viability dye (Life Technologies) according the manufacturer's instructions. Cells were then be incubated for 10 min in blocking solution containing 5% fetal bovine serum in PBS at 4° C. to block Fc receptors. Following that, the cells were stained with a standard panel of immunophenotyping surface antibodies (Table 6) (eBioscience) for 30 minutes at room temperature. After staining, cells were washed with flow buffer and fixed with 2% paraformaldehyde in PBS. Data were acquired with a BD LSRII flow cytometer using BD FACS Diva software (BD Bioscience). Data were analyzed using Flowjo v10.

TABLE 6

| Panel of immunophenotyping antibodies (Mouse) | |
|---|---|
| Antibody | Conjugate |
| CD3 | PE-Cy7 |
| CD4 | Pacific Blue |
| CD8 | APC |
| NK1.1 | PE |
| CD19 | Percp-Cy5.5 |
| CD25 | FITC |
| GR-1 | APC |
| F4/80 | Cy7 |
| CD11b | Percp-Cy5.5 |

Figure 19:
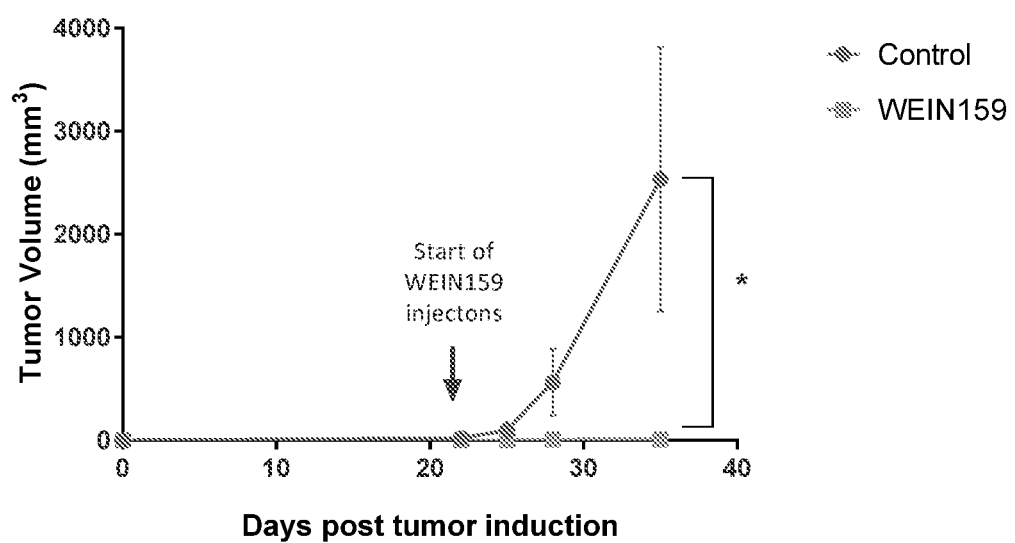
FIG. 19 shows the result from TRAMP-C2 cells implanted subcutaneously in C57BL/6 mice. When tumors became palpable, mice were injected either with vehicle (5% cyclodextrin+10% DMSO in water) or WEIN159 (30 mg/kg of body weight) for 5 days a week for 2 weeks (n=4 for control and n=5 for treatment group). Tumor volumes were measured with calipers. Data are represented as mean±SEM. *p<0.05.
Figure 20A:
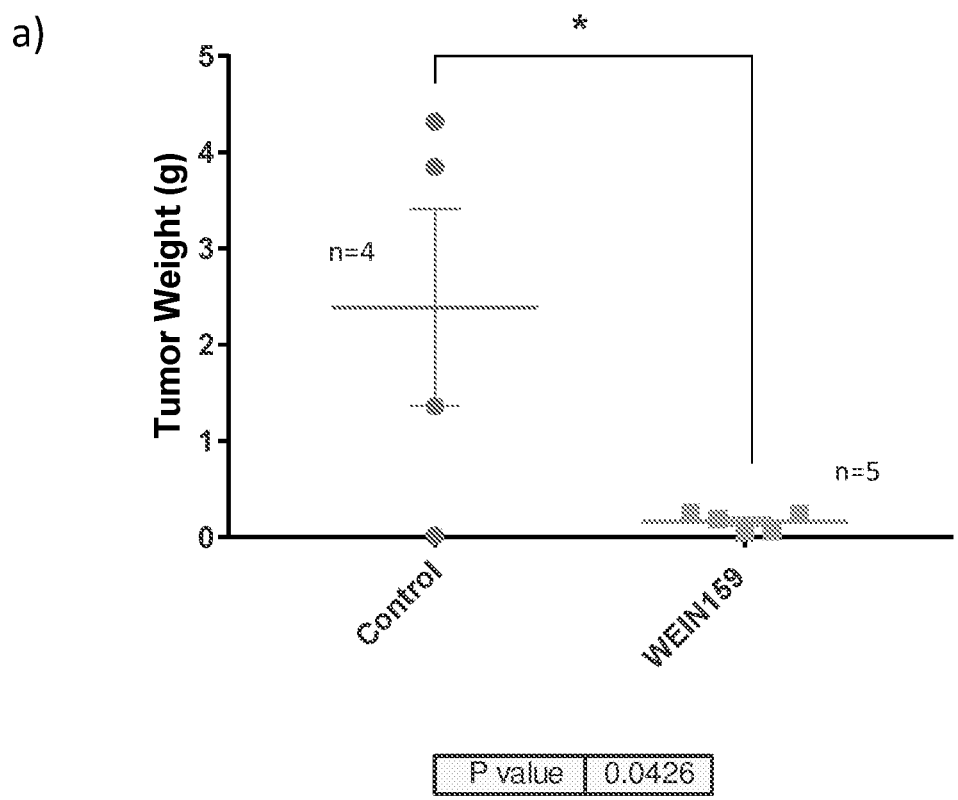
FIG. 20 shows syngenic tumors. The weights (FIG. 20A) and images (FIG. 20B) of TRAMP-C2 tumors injected either with vehicle (5% cyclodextrin+10% DMSO in water) or WEIN159 (30 mg/kg of body weight) for 5 days a week for 2 weeks (n=4 for control and n=5 for treatment group). Data are represented as mean±SEM. *p<0.05.
Figure 20B:
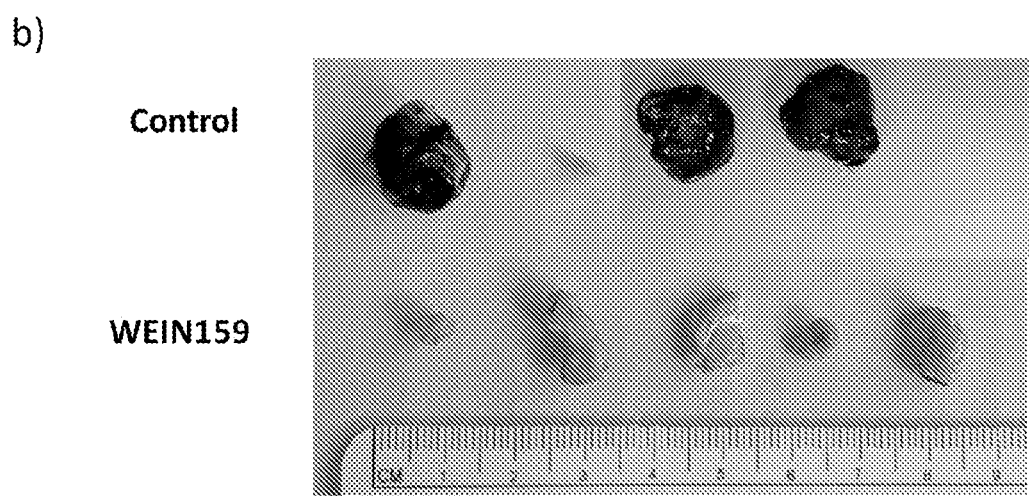
Figure 21A:
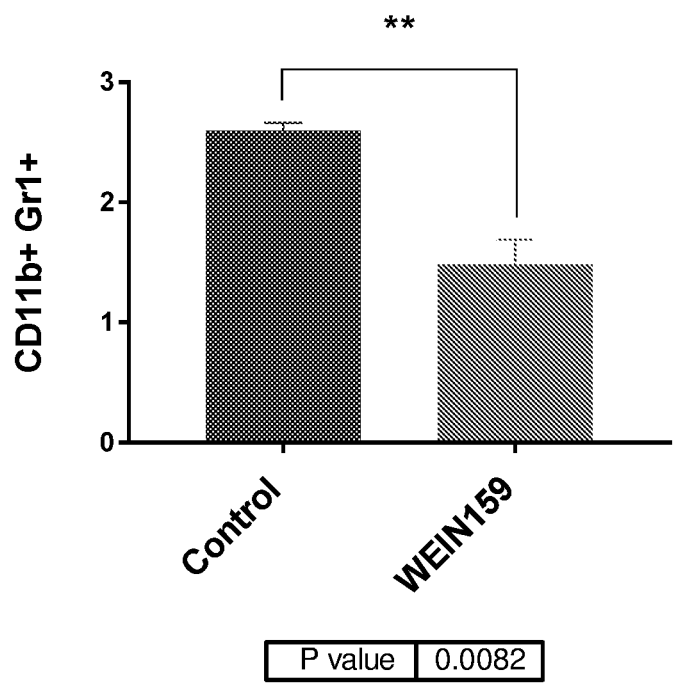
FIG. 21A is a graph showing MDSCs from the spleen. Splenocytes were isolated from TRAMP-C2 tumor bearing mice treated with either vehicle (5% cyclodextrin+10% DMSO in water) or WEIN159 (30 mg/kg of body weight) for 5 days a week for 2 weeks (n=4 for control and n=5 for treatment group).
Figure 21B:
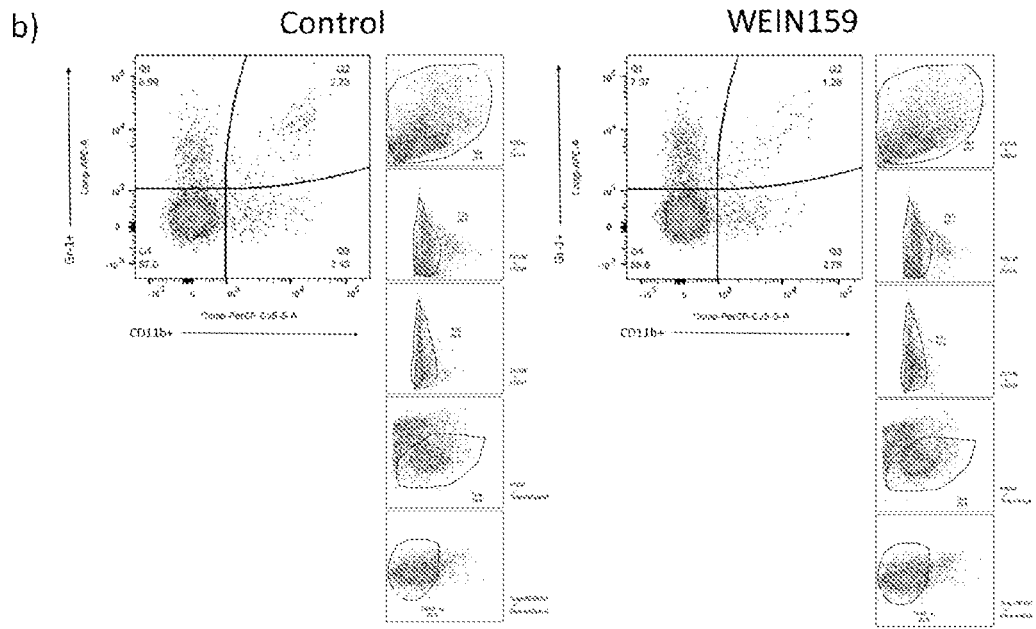
FIG. 21B shows the expression level of Gr-1 on CD11b+ cells, analyzed by flow cytometry. Data are represented as mean±SEM. **p<0.01. Representative scatter plots showing frequency of MDSC subsets in control and WEIN159 treated mice.

Results: Upon testing the efficacy of WEIN159 against tumor growth in C57BL/6 mice bearing sub-cutaneous TRAMP-C2 tumors, it was observed that the tumor growth has been significantly reduced in the drug-treated mice when compared to the control group (See FIGS. 19 and 20). Most tumors have increased levels of myeloid-derived suppressor cells (MDSCs) that is directly proportional to the metastatic burden and poor prognosis. MDSCs are the immunosuppressive subset of myeloid cells found in inflamed tissues. Based on studies, it was reasoned that WEIN-159 could be a promising kinase inhibitor possessing immune modulatory potential that could overcome the major hurdle of suppression of antigen specific T cell responses to immune therapy imparted by MDSCs. Analysis of various cellular components of the immune system showed a significant reduction in the levels of myeloid-derived suppressor cells (MDSCs) in the WEIN-159 treated mice when compared to the control (See FIG. 21).

It was observed that WEIN-159 broadens the scope of application of kinase inhibitors in therapy and current results will have significant implications for ongoing research to control the short comings of cancer immunotherapy.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A compound having a structure below:

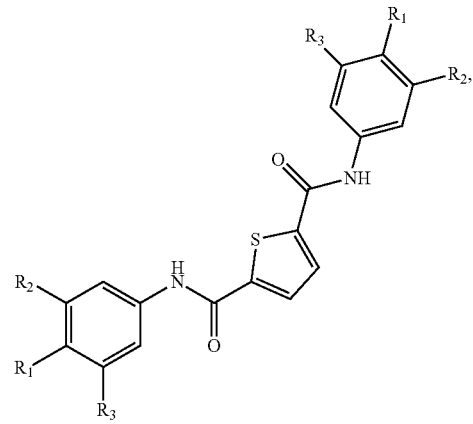

wherein:
$R^1$ is —$NH_2$ or a salt thereof; and
$R_2$ and $R_3$ are independently for each occurrence selected from hydrogen, hydroxyl, $C_1$-$C_6$ alkyl, halogen, amino, $C_{1-6}$ alkyl amine, or a salt thereof.

2. The compound of claim 1, having a structure below:

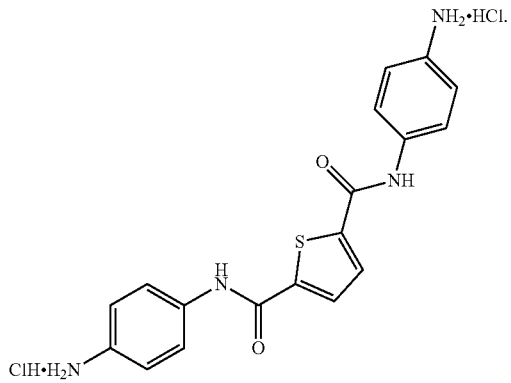

3. A method for inhibiting a WEE1 epigenetic activity, the method comprising administering an effective amount of a compound according to claim 1.

4. A method for treating cancer having WEE1 epigenetic activity in a subject, the method comprising administering to the subject an effective amount of a compound according to claim 1.

5. The method of claim 4, wherein the cancer is glioblastoma (GBM), melanoma, prostate or triple negative breast cancers.

* * * * *